(12) United States Patent
Thibodeau et al.

(10) Patent No.: US 8,426,381 B2
(45) Date of Patent: Apr. 23, 2013

(54) POLYSACCHARIDES COMPOSITIONS COMPRISING FUCANS AND GALACTANS AND THEIR USE TO REDUCE EXTRAVASATION AND INFLAMMATION

(75) Inventors: Alain Thibodeau, St-Augustin (CA); Alain Lavoie, Sainte-Foy (CA); Patrice Dionne, St-Rédempteur (CA); Jean-Yves Moigne, Ile d'Ouessant (FR)

(73) Assignee: Lucas Meyer Cosmetics Canada Inc., Quebec (CA)

( * ) Notice: Subject to any disclaimer, the term of this patent is extended or adjusted under 35 U.S.C. 154(b) by 718 days.

(21) Appl. No.: 11/992,182

(22) PCT Filed: Sep. 11, 2006

(86) PCT No.: PCT/CA2006/001496
§ 371 (c)(1),
(2), (4) Date: Apr. 20, 2009

(87) PCT Pub. No.: WO2007/028256
PCT Pub. Date: Mar. 15, 2007

(65) Prior Publication Data
US 2009/0215720 A1    Aug. 27, 2009

Related U.S. Application Data

(60) Provisional application No. 60/715,178, filed on Sep. 9, 2005, provisional application No. 60/762,488, filed on Jan. 27, 2006.

(51) Int. Cl.
*A61K 31/715* (2006.01)
*A61K 31/70* (2006.01)
*A01N 43/04* (2006.01)

(52) U.S. Cl.
USPC .............................................. 514/54; 514/25

(58) Field of Classification Search ............... 514/54, 514/25
See application file for complete search history.

(56) References Cited

U.S. PATENT DOCUMENTS 3,773,523 A * 11/1973 Chhuy et al. ............... 426/574
5,321,133 A    6/1994 Colliec et al.
6,232,302 B1 * 5/2001 Alberico et al. ............ 514/54
2003/0054015 A1 * 3/2003 Haze et al. ............. 424/195.18

FOREIGN PATENT DOCUMENTS

| WO | WO 2004/105737 | 12/2004 |
| WO | WO 2004105737 | * 12/2004 |
| WO | PCT/CA2006/001496 | 1/2007 |
| WO | PCT/CA2006/001496 | 3/2008 |

OTHER PUBLICATIONS

Damonte et al., Current Medicinal Chemistry, 2004, 11, 2399-2419.*
Haslin et al., Botanica Marina, 2000,43, 475-482.*
Gove et al., Webster's Third New International Dictionary, 1963, p. 1798.*
"Skin disorders", Merck Manual Online Edition, [retrieved on May 2, 2012]. Retrieved from the Internet http://www.merckmanuals.com/home/print/skin_disorders. Revision Aug. 2007 and Oct. 2008.*
Andrade et al., "Ultrastructure of Acidic Polysaccharides from the Cell Walls of Brown Algae", Journal of Structural Biology 145 (2004) pp. 216-225.
Ashida et al., "Involvement of EGF Receptor Activation in the Induction of Cyclooxygenase-2 in HaCaT Keratinocytes after UVB", Experimental Dermatology 12 (2003) pp. 445-452.
Baba et al., "Sulfated Polysaccharides as Potent Inhibitors of HIV-Induced Syncytium Formation: A New Strategy Towards AIDS Chemotherapy", Journal of Acquired Immune Deficiency Syndromes 3 (1990) pp. 493-499.
Bachelor et al., "UVA-Mediated Activation of Signaling Pathways Involved in Skin Tumor Promotion and Progression", Seminars in Cancer Biology 14 (2004) pp. 131-138.
Ballaun et al., "Human Keratinocytes Express the Three Major Splice Forms of Vascular Endothelial Growth Factor", Journal of Investigative Dermatology 104 (1995) pp. 7-10.
Batey et al., "The Galactan Sulphate of the Red Alga *Polysiphonia lanosa*", Carbohydrate Research 43 (1975) pp. 133-143.
Belford et al., "Investigation of the Ability of Several Naturally Occurring and Synthetic Polyanions to Bind to and Potentiate the Biological Activity of Acidic Fibroblast Growth Factor", Journal of Cellular Physiology 157 (1993) pp. 184-189.
Berteau et al., "Sulfated Fucans, Fresh Perspectives: Structures, Functions, and Biological Properties of Sulfated Fucans and an Overview of Enzymes Active Toward this Class of Polysaccharide", Glycobiology 13 (2003) pp. 29R-40R.
Bilan et al., "A Highly Regular Fraction of a Fucoidan from the Brown Seaweed *Fucus distichus* L.", Carbohydrate Resarch 339 (2004) pp. 511-517.

(Continued)

Primary Examiner — Eric S Olson
Assistant Examiner — Zhengfu Wang
(74) Attorney, Agent, or Firm — Wells St. John P.S.

(57) ABSTRACT

A use of an anti-inflammatory polysaccharides composition comprising fucans and galactans to inhibit the release of one or more of IL-8, PGE2 and VEGF by a cell activated during an inflammatory process and an anti-inflammatory composition comprising a ratio of brown algae fucans/red algae galactans of between about 2.5/1 (w/w) to about 40/1 (w/w), the galactans having a molecular weight higher than about 100 kDa, and the fucans having a molecular weight between about 0.1 kDa and 100 kDa.

40 Claims, 4 Drawing Sheets

OTHER PUBLICATIONS

Bilan et al., "Structure of a Fucoidan from the Brown Seaweed *Fucus evanescens* C.Ag.", Carbohydrate Research 337 (2002) pp. 719-730.

Blondin et al., "Inhibition of Complement Activation by Natural Sulfated Polysaccharides (Fucans) from Brown Seaweed", Molecular Immunology 31 (1994) pp. 247-253.

Brauchle et al., "Ultraviolet B and H2O2 are Potent Inducers of Vascular Endothelial Growth Factor Expression in Cultured Keratinocytes", Journal of Biological Chemistry 271 (1996) pp. 21793-21797.

Brennan et al., "Matrix Metalloproteinase-1 is the Major Collagenolytic Enzyme Responsible for Collagen Damage in UV-Irradiated Human Skin", Photochemistry and Photobiology 78 (2003) pp. 43-48.

Carlucci et al., "Antiviral Activity of Natural Sulphated Galactans on Herpes Virus Multiplication in Cell Culture", Planta Medica 63 (1997) pp. 429-432.

Cases et al., "Structure of the 'Corallinans'—Sulfated Xylogalactans from *Corallina officinalis*", International Jounal of Biological Marcomolecules 16 (1994) pp. 93-97.

Chabot-Fletcher et al., "Interleukin-8 Production is Regulated by Protein Kinase C in Human Keratinocytes", Journal of Investigative Dermatology 103 (1994) pp. 509-515.

Cheng et al., "Prostaglandin E2 Induces Vascular Endothelial Growth Factor and Basic Fibroblast Growth Factor mRNA Expression in Cultured Rat Muller Cells", Investigative Ophthalmology and Visual Science 39 (1998) pp. 581-591.

Chevolot et al., "A Disaccharide Repeat Unit is the Major Structure in Fucoidans from Two Species of Brown Algae", Carbohydrate Research 330 (2001) pp. 529-535.

Chizhov et al., "A Study of Fucoidan from the Brown Seaweed *Chorda filum*", Carbohydrate Research 320 (1999) pp. 108-119.

Colliec et al., "A Low Molecular Weight Fucoidan Fraction from the Brown Seaweed *Pelvetia canaliculata*", Phytochemistry 35 (1994) pp. 697-700.

Colliec et al., "Anticoagulant Properties of a Fucoidan Fraction", Thrombosis Research 64 (1991) pp. 143-154.

Coombe et al., "Analysis of the Inhibition of Tumour Metastasis by Sulphated Polysaccharides", International Journal of Cancer 39 (1987) pp. 82-90.

Crawford et al., "Rosacea: I. Etiology, Pathogenesis, and Subtype Classification", Journal of American Academic Dermatology 51 (2004) pp. 327-341.

Damonte et al., "Sulfated Seaweed Polysaccharides as Antiviral Agents", Current Medecinal Chemistry 11 (2004) pp. 2399-2419.

Desai et al., "Loxosceles Deserta Spider Venom Induces the Expression of Vascular Endothelial Growth Factor (VEGF) in Keratinocytes", Inflammation 24 (2000) pp. 1-9.

Detmar et al., "Hypoxia Regulates the Expression of Vascular Permeability Factor/Vascular Endothelial Growth Factor (VPF/VEGF) and its Receptors in Human Skin", Journal of Investigative Dermatology 108 (1997) pp. 263-268.

Detmar et al., "Increased Microvascular Density and Enhanced Leukocyte Rolling and Adhesion in the Skin of VEGF Transgenic Mice", Journal of Investigative Dermatology 111 (1998) pp. 1-6.

Duarte et al., "Inhibitory Effect of Sulfated Galactans from the Marine Alga *Bostrychia montagnei* on Herpes Simplex Virus Replication in Vitro", Carbohydrate Research 339 (2004) pp. 335-347.

Duarte et al., "Structural Studies on Fucoidans from the Brown Seaweed *Sargassum stenophyllum*", Carbohydrate Research 333 (2001) pp. 282-293.

Duarte et al., "The Structure of the Agaran Sulfate from *Acanthophora spicifera* (Rhodomelaceae, Ceramiales) and its Antiviral Activity Relation Between Structure and Antiviral Activity in Agarans", Phytomedicine 8 (2001) pp. 53-58.

Dvorak et al., "Vascular Permeability Factor/Vascular Endothelial Growth Factor, Microvascular Hyperpermeability, and Angiogenesis", American Journal of Pathology 146 (1995) pp. 1029-1039.

Eckes et al., "Regulation of Connective Tissue Homeostasis in the Skin by Mechanical Forces", Clinical and Experimental Rheumatology 22 (2004) pp. S73-S76.

Ellauoli et al., "Antitumor Activity of Low Molecular Weight Fucans Extracted from Brown Seaweed *Ascophyllum nodosum*", Anticancer Research 13 (1993) pp. 2011-2020.

Estevez et al., "DL-Galactan Hybrids and Agarans from Gametophytes of the Red Seaweed *Gymnogongrus torulosus*", Carbohydrate Research 331 (2001) pp. 27-41.

Farias et al., "Dual Effects of Sulfated D-galactans from the Red Algae *Botryocladia occidentalis* Preventing Thrombosis and Inducing Platelet Aggregation", Journal of Thrombosis and Haemostasis 86 (2001) pp. 1540-1546.

Farias et al., "Structure and Anticoagulant Activity of Sulfated Galactans", Journal of Biological Chemistry 275 (2000) pp. 29299-29307.

Ferrao et al., "The Effect of Heparin on Cell Proliferation and Type-I Collagen Synthesis by Adult Human Dermal Fibroblasts", Biochimica et Biophysica Acta 1180 (1993) pp. 225-230.

Finkel et al., "Oxidants, Oxidative Stress and the Biology of Ageing", Nature 408 (2000) pp. 239-247.

Fisher et al., "Mechanisms of Photoaging and Chronological Skin Aging", New England Journal of Medicine 337 (1997) pp. 1419-1428.

Fisher et al., "Pathophysiology of Premature Skin Aging Induced by Ultraviolet Light", Archives of Dermatology 138 (2002) pp. 1462-1470.

Fisher, "The Pathophysiology of Photoaging of the Skin", CUTIS 75 (2005) pp. 5-9.

Freile-Pelegrin et al., "Agars from Three Species of *Gracilaria* (Rhodophyta) from Yucatan Peninsula", Bioresource Technology 96 (2005) pp. 295-302.

Geresh et al., "Sulfation of Extracellular Polysaccharides of Red Microalgae: Preparation, Characterization and Properties", Journal of Biochemical and Biophysical Methods 50 (2002) pp. 179-187.

Gille et al., "Ultraviolet-A-Induced Transactivation of the Vascular Endothelial Growth Factor Gene in HaCaT Keratinocytes is Conveyed by Activator Protein-2 Transcription Factor", Journal of Investigative Dermatology 115 (2000) pp. 30-36.

Glabe et al., "Reversible Disruption of Cultured Endothelial Monolayers by Sulphated Fucans", Journal of Cell Science 61 (1983) pp. 475-490.

Gove et al., "Webster's Third New International Dictionary of the English Language (Unabridged)", Merriam-Webster, p. 1798, 1963.

Granert et al., "Inhibition of Leukocyte Rolling with Polysaccharide Fucoidin Prevents Pleocytosis in Experimental Meningitis in the Rabbit", Journal of Clinical Investigation 93 (1994) pp. 929-936.

Hahnenberger et al., "Antiangiogenic Effect of Sulphated and Nonsulphated Glycosaminoglycans and Polysaccharides in the Chick Embryo Chorioallantoic Membrane", Glycoconjugate Journal 8 (1991) pp. 350-353.

Harada et al., "Induction of Vascular Endothelial Growth Factor Expression by Prostaglandin E2 and E1 in Osteoblasts", Journal of Clinical Investigation 93 (1994) pp. 2490-2496.

Harhaj et al., "Regulation of Tight Junctions and Loss of Barrier Function in Pathophysiology", International Journal of Biochemistry and Cell Biology 36 (2004) pp. 1206-1237.

Haslin et al., "Chemical Composition and Structure of Sulphated Water-Soluble Cell-Wall Polysaccharides from the Gametic, Carposporic and Tetrasporic Stages of *Asparagopsis armata* Harvey (Rhodophyta, Bonnemaisoniaceae)", Botanica Marina 43 (2000) pp. 475-482.

Haslin et al., "In Vitro Anti-HIV Activity of Sulfated Cell-Wall Polysaccharides from Gametic, Carposporic and Tetrasporic Stages of the Mediterranean Red Alga *Asparagopsis armata*", Planta Medica 67 (2001) pp. 301-305.

Hruza et al., "Mechanisms of UV-Induced Inflammation", Journal of Investigative Dermatology 100 (1993) pp. 35S-41S.

Huleihel et al., "Spectroscopic Evaluation of the Effect of a Red Microalgal Polysaccharide on Herpes-Infected Vero Cells", Applied Spectroscopy 57 (2003) pp. 390-395.

Jenkins et al., "Molecular Mechanisms of Skin Ageing", Mechanisms of Ageing and Development 123 (2002) pp. 801-810.

Kabashima et al., "Prostanoids in the Cutaneous Immune Response", Journal of Dermatological Science 34 (2004) pp. 177-184.

Kariya et al., "Isolation and Partial Characterization of Fucan Sulfates from the Body Wall of Sea Cucumber *Stichopus japonicus* and their Ability to Inhibit Osteoclastogenesis", Carbohydrate Research 299 (2004) pp. 1339-1346.
Kessler et al., "Fibroblasts in Mechanically Stressed Collagen Lattices Assume a "Synthetic" Phenotype", The Journal of Biological Chemistry 276 (2001) pp. 36575-36585.
Kolander et al., "Sulfated Polysaccharides from the Red Seaweed *Georgiella confluens*", Carbohydrate Research 337 (2002) pp. 57-68.
Kosmadaki et al., "UV Induces VEGF Through a TNF-Alpha Independent Pathway", Federation of American Societies for Experimental Biology Journal 17 (2003) pp. 466-468.
Lachgar et al., "Inhibitory Effects of Retinoids on Vascular Endothelial Growth Factor Production by Cultured Human Skin Keratinocytes", Dermatology 199 (1999) pp. 25-27.
Lee et al., "Cyclooxygenases in the Skin: Pharmacological and Toxicological Implications", Toxicology and Applied Pharmacology 192 (2003) pp. 294-306.
Lee et al., "Novel Antiviral Fucoidan from Sporophyll of *Undaria pinnatifida* (Mekabu)", Chemical and Pharmeceutical Bulletin 52 (2004) pp. 1091-1094.
Lewis et al., "Acquired Disorders of Elastic Tissue: Part I. Increased Elastic Tissue and Solar Elastotic Syndromes", American Academy of Dermatology 51 (2004) pp. 1-21.
Lewis et al., "Acquired Disorders of Elastic Tissue: Part II. Decreased Elastic Tissue", American Academy of Dermatology 51 (2004) pp. 165-185.
Li et al., "Toxicological Evaluation of Fucoidan Extracted from *Laminaria japonica* in Wistar Rats", Food and Chemical Toxicology 43 (2005) pp. 421-426.
Liao et al., "Sulfated Galactans from Australian Specimens of the Red Alga *Phacelocarpus peperocarpos* (Gigartinales, Rhodophyta)", Carbohydrate Research 296 (1996) pp. 237-247.
Logeart et al., "Fucans, Sulfated Polysaccharides Extracted from Brown Seaweeds, Inhibit Vascular Smooth Muscle Cell Proliferation. I. Comparison with Heparin for Antiproliferative Activity, Binding and Internalization", European Journal of Cell Biology 74 (1997) pp. 376-384.
Longuet-Perret et al., "Tumour Necrosis Factor-a is Involved in the Contrasting Effects of Ultraviolet B and Ultraviolet A1 Radiation on the Release by Normal Human Keratinocytes of Vascular Permeability Factor", British Journal of Dermatology 138 (1998) pp. 221-224.
Luepke et al., "Hen's Egg Chorioallantoic Membrane Test for Irritation Potential", Chemical Toxicology 2 (1985) pp. 287-291.
Mabeau et al., "Fractionation and Analysis of Fucans from Brown Algae", Phytochemistry 29 (1990) pp. 2441-2445.
Mahony et al., "Fucoidin Binding Activity and its Localization on Human Spermatozoa", Contraception 48 (1993) pp. 277-289.
Marais et al., "A Fucoidan Fraction from *Ascophyllum nodosum*", Carbohydrate Research 336 (2001) pp. 155-159.
Marinho-Soriano et al., "Polysaccharides from the Red Seaweed *Gracilaria dura* (Gracilariales, Rhodophyta)", Bioresource Technology 96 (2005) pp. 379-382.
Matsumoto et al., "Fucoidan Derived from *Cladosiphon okamuranus* Tokida Ameliorates Murine Chronic Colitis Through the Down-Regulation of Interleukin-6 Production on Colonic Epithelial Cells", Clinical and Experimental Immunology 136 (2004) pp. 432-439.
Matsumura et al., "Short-Term and Long-term Cellular and Molecular Events Following UV Irradiation of Skin: Implications for Molecular Medicine", Expert Reviews in Molecular Medicine (2002) pp. 1-22.
Matsumura et al., "Toxic Effects of Ultraviolet Radiation on the Skin" Toxicology and Applied Pharmacology 195 (2004) pp. 298-308.
Mauray et al., "Venous Antithrombotic and Anticoagulant Activities of a Fucoidan Fraction", Thrombosis and Haemostasis 74 (1995) pp. 1280-1285.
Melo et al., "Antithrombin-Mediated Anticoagulant Activity of Sulfated Polysaccharides: Different Mechanisms for Heparin and Sulfated Galactans", Journal of Biological Chemistry 279 (2004) pp. 20824-20835.
Midwood et al., "Tissue Repair and the Dynamics of the Extracellular Matrix", The International Journal of Biochemistry and Cell Biology 36 (2004) pp. 1031-1037.
Nagaoka et al., "Structural Study of Fucoidan from *Cladosiphon okamuranus* TOKIDA", Glycoconjugate Journal 16 (1999) pp. 19-26.
Nickoloff et al., "Aberrant Production of Interleukin-8 and Thrombospondin-1 by Psoriatic Keratinocytes Mediates Angiogenesis", American Journal of Pathology 144 (1994) pp. 820-828.
Nishino et al., "Anticoagulant and Antithrombin Activities of Oversulfated Fucans", Carbohydrate Research 229 (1992) pp. 355-362.
Nishino et al., "Structural Characterization of a New Anticoagulant Fucan Sulfate from the Brown Seaweed *Ecklonia kurome*", Carbohydrate Research 211 (1991) pp. 77-90.
Pereira et al., "Structure and Anticoagulant Activity of Sulfated Fucans: Comparison Between the Regular, Repetitive, and Linear Fucans from Echinoderms with the More Heterogeneous and Branched Polymers from Brown Algae", The Journal of Biological Chemistry 274 (1999) pp. 7656-7667.
Ponce et al., "Fucoidans from the Brown Seaweed *Adenocystis utricularis*: Extraction Methods, Antiviral Activity and Structural Studies", Carbohydrate Research 338 (2003) pp. 153-165.
Preobrazhenskaya et al., "Fucoidan Inhibits Leukocyte Recruitment in a Model Peritonial Inflammation in Rat and Blocks Interaction of P-Selectin with its Carbohydrate Ligand", Biochemistry and Molecular Biology International 43 (1997) pp. 443-451.
Rhodes et al., "Ultraviolet-B-Induced Erythema is Mediated by Nitric Oxide and Prostaglandin E2 in Combination", Journal of Investigative Dermatology 117 (2001) pp. 880-885.
Rijken et al., "Skin-Infiltrating Neutrophils Following Exposure to Solar-Simulated Radiation Could Play an Important Role in Photoageing of Human Skin", British Journal of Dermatology 152 (2005) pp. 321-328.
Riou et al., "Antitumor and Antiproliferative Effects of a Fucan Extracted from *Ascophyllum nodosum* Against a Non-Small-Cell Bronchopulmonary Carcinoma Line", Anticancer Research 16 (1996) pp. 1213-1218.
Ruperez et al., "Potential Antioxidant Capacity of Sulfated Polysaccharides from the Edible Marine Brown Seaweed *Fucus vesiculosus*", Journal of Agricultural and Food Chemistry 50 (2002) pp. 840-845.
Sakai et al., "A Marine Strain of Flavobacteriaceae Utilizes Brown Seaweed Fucoidan", Marine Biotechnology 4 (2002) pp. 399-405.
Sakai et al., "Structures of Oligosaccharides Derived from *Cladosiphon okamuranus* Fucoidan by Digestion with Marine Bacterial Enzymes", Marine Biotechnology 5 (2003) pp. 536-544.
Schaller et al., "Induction of a Chemoattractive Proinflammatory Cytokine Response After Stimulation of Keratinocytes with Propionibacterium Acnes and Coproporphyrin III", British Journal of Dermatology 153 (2005) pp. 66-71.
Seo et al., "Enhanced Expression of Cylooxygenase-2 by UV in Aged Human Skin in Vivo", Mechanisms of Ageing and Development 124 (2003) pp. 903-910.
Silver et al., "Mechanosensing and Mechanochemical Transduction: How Is Mechanical Energy Sensed and Converted into Chemical Energy in an Extracellular Matrix?", Critical Reviews in Biomedical Engineering 31 (2003) 255-331.
Soeda et al., "Preparation of Oversulfated Fucoidan Fragments and Evaluation of Their Antithrombotic Activities", Thrombosis Research 72 (1993) pp. 247-256.
Soter, "Acute Effects of Ultraviolet Radiation on the Skin", Seminars in Dermatology 9 (1990) pp. 11-15.
Stevan et al., "Cytotoxic Effects Against HeLa Cells of Polysaccharides from Seaweeds", Journal of Submicroscopic Cytology and Pathology 33 (2001) pp. 477-484.
Tissot et al., "Interaction of Fucoidan with the Proteins of the Complement Classical Pathway", Biochimica et Biophysica Acta 165 (2003) pp. 5-16.

Trompezinski et al., "Comparative Expression of Vascular Endothelial Growth Factor Family Members, VEGF-B, -C and -D, by Normal Human Keratinocytes and Fibroblasts", Experimental Dermatology 13 (2004) pp. 98-105.

Trompezinski et al., "UV Radiation and Prostaglandin E2 Up-Regulate Vascular Endothelial Growth Factor (VEGF) in Cultured Human Fibroblasts", Journal of Inflammation Research 50 (2001) pp. 422-427.

Usov et al., "Polysaccharides from Algae. 51. Partial Reductive Hydrolysis of Sulfated Galactan from Red Alga *Laurencia coronopus* J. Ag. (Rhodophyta, Rhodomelaceae)", Advances in Carbohydrate Chemistry and Biochemistry 41 (1983) pp. 27-66.

Usov et al., "Structure of a Sulfated Xylogalactan from the Calcareous Red Alga *Corallina pilulifera* P. et R. (Rhodophyta, Corallinaceae)", Carbohydrate Research 303 (1997) pp. 93-102.

Van Zuuren et al., "The Cochrane Collaboration: Interventions for Rosacea (Review)", Cochrane Database System Review 20 (2004) 94 pages.

Varani et al., "Reduced Fibroblast Interaction with Intact Collagen as a Mechanism for Depressed Collagen Synthesis in Photodamaged Skin", The Journal of Investigative Dermatology 122 (2004) pp. 1471-1479.

Wells et al., "Overview of Sunlight and Skin Damage", Merck Manual Home Edition: Skin Disorders (Last Review 2008) 5 pages.

Wilkin et al., "Rosacea: Pathophysiology and Treatment", Arch Dermatol 130 (1994) pp. 359-362.

Yano et al., "A Novel Mechanism of Skin-Aging Mediated by UV-Induced Angiogenesis, and Inhibitory Effects of Natural Compounds on UV-Induced Angiogenesis", 23rd IFSCC Congress (2004) pp. 46-51 (Abstract).

Yano et al., "Ultraviolet B Irradiation of Human Skin Induces an Angiogenic Switch that is Mediated by Upregulation of Vascular Endothelial Growth Factor and by Downregulation of Thrombospondin-1", British Journal of Dermatology 152 (2005) pp. 115-121.

Yu-Ping et al., "Transgenic Delivery of VEGF to Mouse Skin Leads to an Inflammatory Condition Resembling Human Psoriasis", Blood 102 (2003) pp. 161-168.

Zhang et al., "Fucoidan Inhibits the Development of Proteinuria in Active Heymann Nephritis", Pytotherapy Research 19 (2005) pp. 50-53.

Zhang et al., "The Structure of a Sulfated Galactan from *Porphyra haitanensis* and its in Vivo Antioxidant Activity", Carbohydrate Research 339 (2004) pp. 105-111.

Zhou et al., "In Vivo Antitumor and Immunomodulation Activities of Different Molecular Weight Lambda-Carrageenans from *Chondrus ocellatus*", Pharmacological Research 50 (2004) pp. 47-53.

Zhu et al., "Isolation and Characterization of a Sulfated Polysaccharide from the Brown Alga *Sargassum patens* and Determination of its Anti-Herpes Activity", Biochemistry and Cell Biology 81 (2003) pp. 25-33.

Zhuang et al., "Antitumor Active Fucoidan from the Brown Seaweed, Umitoranoo (*Sargassum thunbergii*)", Bioscience, Biotechnology, and Biochemistry 59 (1995) pp. 563-567.

Zvyagintseva et al., "Inhibition of Complement Activation by Water-Soluble Polysaccharides of Some Far-Eastern Brown Seaweeds", Comparative Biochemistry and Physiology Part C 126 (2000) pp. 209-215.

\* cited by examiner

POLYSACCHARIDES COMPOSITIONS COMPRISING FUCANS AND GALACTANS AND THEIR USE TO REDUCE EXTRAVASATION AND INFLAMMATION

CROSS REFERENCE TO RELATED APPLICATIONS

This application is a National Entry Application of PCT application No. PCT/CA2006/001496 filed on 11 Sep. 2006 and published in English under PCT Article 21(2), which itself claims priority on U.S. provisional application no. 60/715,178, filed on 9 Sep. 2005 and on U.S. provisional application no. 60/762,488, filed on 27 Jan. 2006. All documents above are herein incorporated by reference.

FIELD OF THE INVENTION

The present invention relates to polysaccharides compositions comprising fucans and galactans and their use to reduce extravasation and inflammation. More specifically, the present invention is concerned with use of polysaccharide compositions comprising fucans and galactans obtained from brown and red algae, respectively, which have anti-inflammatory and vascular protective activities. The invention also relates to a method for treating, preventing or alleviating the symptoms of disorders and diseases associated with excess levels of pro-inflammatory mediators, extravasation stimulating agents and consequent vascular and extracellular effects. Amongst these diseases or disorders are those affecting skin, caused by UV, pollutants exposure, stress, psoriasis, acne, rosacea, skin cancer, and/or skin aging.

BACKGROUND OF THE INVENTION

Fucans are polysaccharides originating mainly from the cell walls of shoots of brown algae (Pheophyceae family) belonging to the *Ascophyllum, Fucus, Pelvetia* and *Himmanthali* genera. They are also found in some marine animals, such as sea urchins and sea cucumbers. Fucans obtained by extraction from the cell walls of brown algae shoots, also termed fucoidans when in their sulfated form, consist of a heterogeneous population of molecules which comprises principally sulfated L-fucose polymers of average molar mass ranging from 5000 to 800,000 g/mol. These polymers also contain uronic acids. Whilst sulfatation degree, molecular weight, and structure of sugar residues of fucans vary among species, several studies clearly show that brown algae fucans, for example, *Ascophyllum nodosum* fucans possess a large portion of both α(1→3) and α(1→4) glycosidic bonds.

Fucans have varied biological activities: it was shown that they have anticoagulant and antithrombotic activities (T. Nishino and T. Nagumo, Carbohydr. Res. 229, p. 355-362, (1992); Application EP 0403 377; S. Colliec et al. Thromb. Res. 64, p. 143-154 (1991); S. Soeda et al. Thromb. Res. 72, p. 247-256 (1993); Mauray et al. Thromb. Haemost. (5) 1280-1285 (1995)), they can protect cells against viral infection (M. Baba et al. J. AIDS, 3, p. 493-499, (1990)), they have antiangiogenic (R. Hahnenberger and A. M. Jackobson, Glycoconjugate J., 8, 350-353 (1991)) and anticomplementary (C. Blondin et al., Mol. Immunol., 31, p. 247-253, (1994)) activities. It has also been observed that they can act as modulators of cell adhesion (C. G. Glabe et al., J. Cell Sci., 61, p. 475-490, (1983)), of growth factor release (D. A. Belfort et al., J. Cell. Physiol. 157, p. 184-189, (1993)), of tumor cell's (M. Ellouali et al., Anticancer Res., 13, p. 2011-2020 (1993); D. R. Coombe et al., Int. J. Cancer, 39, pp. 82-90, (1987); D. Riou et al., Anticancer Res., 16, 1213-1218 (1996)) and of vascular smooth muscle cell's proliferation (Logeart et al., Eur. J. Cell. Biol., 74, pp. 376-384 (1997)), and can block spermatozoid/ovule interactions in various species (M. C. Mahony et al., Contraception; 48, p. 277-289, (1993)).

Galactans are other polysaccharides originating mainly from the cell walls of red algae (Redphyceae family). The most abundant galactans found in the red algae are carrageenans and agarans. These polysaccharides play a significant physiological role in the resistance of mechanical stress, hydration, and in both the ionic and the osmotic regulation required within marine environments. Raw galactans are obtained by extraction from the cell walls of red algae shoots, and consist of a heterogeneous population of molecules which comprises mainly sulfated beta-D-galactose, xylose and galactose polymers of average molar mass ranging from 50,000 to 800,000 g/mol.

Galactans have varied known biological activities: They have anticoagulant (Melo et al., J. Biol. Chem. 279:20824-35(2004); Pereira et al., 1999; Facia et al., J. Biol. Chem. 275:29299-307 (2000)) and antiviral activities (Duarte et al., Carbohydr Res. 339:335-47(2004); Huleihel et al., Appl Spectrosc. 57:390-5. (2003); Carlucci et al., Planta Med. 63:429-32 (1997)). It has also been observed that they can act as modulators of proliferation of tumor cells (Zhou et al., Pharmacol. Res. 50:47-53 (2004); Geresh et al J Biochem Biophys Methods. 50:179-87 (2002)).

Processes for obtaining fucans and galactans from a plurality of species have been summarized in Tables 1 and 2, respectively. Generally, brown algae are good sources of fucans while red algae are good sources of galactans.

TABLE 1

BROWN ALGAE AS SOURCES OF SULFATED-FUCANS AND KNOWN PROCESSES FOR THEIR OBTENTION

| Species | References |
| --- | --- |
| *Ascophyllum nodosum* | Marais and Joseleau (Carbohydr. Res 336: 155-159; 2001), Mabeau et al. Phytochemistry 29: 2441-2445; 1990), Pereira et al. (J. Biol. Chem 274(12): 7656-7667; 1999), Tissot et al. (Biochim. Biophys. Acta 165(1-2): 5-16; 2003) |
| *Fucus* sp. | Chevolot et al. (Carbohydr. Res. 330(4): 529-535; 2001), Bilan et al. (Carbohydr. Res. 337(8): 719-730; 2002)), Bilan et al. (Carbohydr. Res. 339(3): 511-517; 2004), Ruperez et al. (J. Agric. Food Chem. 50(4): 840-845; 2002 |
| *Stichopus japonicus* | Kariya et al. (Carbohydr. Res. 339(7): 1339-1346; 2004) |
| *Sargassum* sp. | Duarte et al. (Carbohydr. Res. 333(4): 282-293; |

TABLE 1-continued

BROWN ALGAE AS SOURCES OF SULFATED-FUCANS AND KNOWN PROCESSES FOR THEIR OBTENTION

| Species | References |
|---|---|
| | 2001), Zhu et al. (Biochem. Cell Biol. 81(1): 25-33; 2003), Zhuang et al. (Biosci. Biotechnol. Biochem. 59(4): 563-567; 1995), Nagaoka et al. (Glycoconj. J. 16: 19-26; 1999) |
| Padina gymnospora | Andrade et al. (J. Struct. Biol. 145(3): 216-225; 2004) |
| Adenocystis utricularis | Ponce et al. (carbohydr. Res 338(2): 153-165: 2003) |
| Cladosiphon okamuranus | Sakai et al. (Mar. Biotechnol. 5(6): 536-544; 2003), Nagaoka et al. (Glycoconj. J. 16: 19-26; 1999) |
| Kjellmaniella crassifolia | Sakai et al. (Mar. Biotechnol. 4(4): 399-405; 2002), Nagaoka et al. (Glycoconj. J. 16: 19-26; 1999) |
| Pelvetia canaliculata | Colliec etal. (Phytochemistry 35: 697-700; 1991) |
| Ecklonia kurome | Nishino et al. (Carbohydr. Res. 211(1): 77-90; 1991) |
| Chorda filum | Chizhov et al. (Carbohydr. Res. 320(1-2): 108-119; 1999) |
| Undaria pinnatifida | Lee et al. (Chem. Pharm. Bull. 52(9): 1091-1094; 2004 |
| Laminaria japonica | Zvyagiintseva et al. (Comp. Bichem. Physiol. C. Toxicol. Pharmacol. 126(3): 209-215; 2000) |

TABLE 2

RED ALGAE AS SOURCES OF GALACTANS AND KNOWN PROCESSES FOR THEIR OBTENTION

| Species | references |
|---|---|
| Asparagopsis sp. | Haslin et al. (Planta Med. 67(4): 301-305; 2001) |
| Bostrychia montagnei | Duarte et al. (Phytomedicine 8(1): 53-58; 2001) |
| Corallina sp. | Usov et al. (Carbohydr. Res. 303(1): 93-102; 1997), Cases et al. (Int. J. Biol. Macromol. 16(2): 93-97; 1994) |
| Polysiphonia lanosa | Batey and Survey (Carbohydr. Res. 43(1): 133-43; 1975) |
| Gracilaria sp. | Marinho-Soriano and Bourret (Bioresour. Technol. 96(3): 379-382; 2005), Freile-Pelegrin and Murano (Bioresour. Technol. 96(3): 295-302; 2005) |
| Acanthophora spicifer | Duarte et al. (Carbohydr. Res. 339(2): 335-347; 2004) |
| Georgiella confluens | Kolander and Matulewicz (Carbohydr. Res. 337(1): 57-68; 2002) |
| Laurencia coronus | Usov et Elashvili (Bioorg. Khim 23(6): 505-511; 1997) |
| Porphyra haitanensis | Zhang et al. (Carbohydr. Res. 339(1): 105-111; 2004) |
| Botryocladia occidentalis | Farias et al. (Thromb. Haemost. 86(6): 1540-1546; 2001), Farias et al. (J. Biol. Chem. 275(38): 29299-29307; 2000) |
| Cryptopleura ramosa | Carlucci et al. (Planta Med. 63(5): 429-432; 1997) |
| Chondrus ocellatus | Zhou et al. (Pharmacol. Res. 50(1): 47-53; 2004) |
| Gymnogongrus tolulosus | Estevez et al. (Carbohydr. Res. 331(1): 27-41; 2001) |
| Phacelocarpus peperocarpos | Liao et al. (Carbohydr. Res; 296: 237-247; 1996) |

Human epithelium plays an essential role in the equilibrium and repair of connective tissues. It is in particular responsible for renewing extracellular matrix (ECM), and in return its functions are modified by the substances present in this matrix.

In particular, in the process of tissue remodeling and healing which intervene after an injury, the connective tissue is the context for constant exchanges between all the cells involved in this process. These exchanges take place in particular via cytokines or soluble mediators which are transmitted through the ECM.

For example, in the covering connective tissues such as the cutaneous tissues, the healing process begins after the formation of a provisional matrix (red thrombus), with the recruitment of inflammatory cells (leukocytes, macrophages and polymorphonuclear cells), which initiate a phase of destruction of the lesioned tissue.

These inflammatory cells participate in the destruction by secreting matrix proteinases such as collagenase (MMP8), leukocytic or neutrophil elastase or cathepsin G, by liberating cytokines, and in particular interleukin-1 (IL-1), which stimulate the proliferation and migration of fibroblasts and of epithelial cells, and the expression, by these cells, of certain metalloproteinases such as interstitial collagenase (MMP1) or gelatinase B (MMP9).

This destruction phase, which begins very soon after the injury, ends when the epithelium and its basement membrane have been reconstituted.

It is followed by repair and resolution phases in which the fibroblasts reconstruct and reorganize the collagen framework; the expression by the fibroblasts of gelatinase A (MMP2) is in particular observed, matrix metalloproteinase actively participating in all the tissue remodeling phenomena.

Repercussion of UV exposure on the skin microcapillary integrity: The cutaneous layer is the primary external barrier protecting the body from harm as a result of invading foreign particles. In order to adequately perform its function, the skin has been endowed with a range of endogenous surveillance systems. Following tissue damage, free radicals are released with active cytokines to counteract these non-self particles. Subsequently, enzymatic activities proceed to dismantle damaged components such as cell bodies and fibrillar components of the ECM. This occurs before repair processes establish and are able to promote cellular proliferation and biosynthetic activity of the ECM's components.

At the microscopic level, the skin may be viewed as a highly complex arrangement of diversified cell types which are embedded within the ECM. In addition to serving as a structural scaffold, the ECM functions as a highway providing the means for cell movement, migration and differentiation. It also functions as a signal transduction pathway through which chemical mediators are able to travel between individual cells and the superposed skin layers. To a certain extent, the skin's ECM may be conceptualized as a loose interlaced cotton weave into which cells are nested and able to interact with one another and their surrounding environment.

The ECM appears as a complex array of macromolecules and fibrillar components. These components are fashioned with various types of collagen fibers, elastin fibers, glycosaminoglycans and glycoproteins. The ECM is both produced and organized by its resident cells; mainly the keratinocytes and fibroblasts. This amalgamated connective tissue is responsible for the firmness, elasticity as well as the overall integrity of the skin. Despite its highly intricate fibrillar composition, the ECM remains a dynamic structure. As such, it must be involved in morphogenesis and tissue repair, thus supporting cell proliferation and macromolecular remodelling. The plasticity of the ECM can further be demonstrated in its role in sensing external mechanical forces.

It has been suggested that the application of tensile, gravitational force and stretching forces to the skin trigger a mechanochemical signal transduction (mechanosensing) involving the direct ECM-cell and/or cell-cell interactions (Silver F H, Siperko L M. Crit Rev Biomed Eng. 2003; 31(4):255-331). Specifically, the ECM network acts as a sensor that informs skin cells on how to adapt to dynamic environmental conditions. Through downstream signal transduction, the skin's ECM may also influence other tissues through their response to external stimuli (Eckes B, Krieg T. Clin Exp Rheumatol. 2004 January-February; 22(3 Suppl 33):S73-6). For instance, the mechanical forces imposed by a tridimensional collagen network switch on "mechanical-responsive genes" that favour a synthetic phenotype (Kessler D, Dethlefsen S, Haase I, Plomann M, Hirche F, Krieg T, Eckes B. J Biol. Chem. 2001 Sep. 28; 276(39):36575-85). This illustrates the ability of the ECM to support both a biochemical role and an obvious physical function as a home for resident cells. As a result of its intimate interaction with the external environment, the ECM and its associated structures are vulnerable to the continuous barrage of external insults. Ultimately, the repeated effects of these insults may affect the skin's health and appearance.

Chronological and actinic aging of the skin: Aging is a multifactorial phenomenon. The aging of the skin is mainly the result of one's genetic predisposition (known as chronological aging) and one's physiological reaction to environmental stresses (known as actinic aging). Chronological aging is largely genetically driven and appears to be mainly a reduction in anti-oxidant production (Finkel T, Holbrook N. J. Nature. 2000 Nov. 9; (408):239-247), cellular senescence and a general lowering of anabolic activities (Jenkins G. Mech Ageing Dev. 2002 April; 123(7):801-10). Actinic aging seems to be skin specific and is defined as the effect of the external environment on the skin's biological response. The skin response to actinic aging, also referred to as photo-damage, is typically associated with a lack of normal hydration, apparition of telangiectasia, sagging of the skin and the appearance of fine line and wrinkles.

Environmental insults, such as UV and/or polluting deleterious chemicals found in the atmosphere are typically encountered by keratinocytes of the epidermis which are located at the outmost peripheral level of the skin. The reaction of keratinocytes to the environmental stimuli triggers a cascade of reactions where the acquisition of the initial signal is passed on from cell to cell through a mechanism of biochemical interpretations. As a result, the ensuing biological response may be amplified and propagated to other layers of the skin. This cascade of biochemical reactions, especially upon UV exposure, is directly correlated to a number of histological damages that accumulate to provoke the appearance of signs of actinic aging.

UV irradiation has been shown to have pleiotropic effects at the skin level causing DNA lesions, cellular apoptosis, immunosuppression and inflammation/erythema (Soter N A. Semin Dermatol. 1990 March; 9(1):11-5, Matsumura Y, Ananthaswamy H N. Expert Rev Mol. Med. 2002 Dec. 2; 2002:1-22). With respect to actinic skin aging—or photo-damage—the increase in matrix metalloproteinase (MMP) activation and expression is the most recognized degradation pathway induced as a result of the skin exposure to UV (Fisher G J. CUTIS. 2005 February; (75):5-9). It has been suggested that the proteolytic action of MMP causes the breakdown of collagen fibers in the ECM and that the histological damages which ensues eventually leads to the appearance of a photo-damaged phenotype (Fisher G J, Wang Z Q, Datta S C, Varani J, Kang S, Voorhees J J. New-England Journal of Medicine. 1997; 337:1419-1428; Fisher G J, Kang S, Varani J, Bata-Csorgo Z, Wan Y, Datta S, Voorhees J J. Arch Dermatol. 2002 November; 138(11):1462-70; Brennan M, Bhatti H, Nerusu K C, Bhagavathula N, Kang S, Fisher G J, Varani J, Voorhees J J. Matrix Photochemistry and Photobiology. 2003; 78(1):43-48). Furthermore, it is suggested that the reduction in the ability of fibroblasts to synthesize collagen is reduced in photo-damaged skin as a result of a decreased cell-ECM mechanical tension (Varani J, Schuger L, Dame M K, Leonard C, Fligiel S E, Kang S, Fisher G J, Voorghees J J. J Invest Dermatol. 2004 June; 122(6):1471-9).

Alteration to the tridimensional organization of the skin's ECM is undoubtedly among the most significant and apparent molecular changes during actinic aging. This microscopic modification ultimately results in the macroscopic appearance of cutaneous aging. Those changes triggered during actinic aging involve the release of biochemical mediators that have pleiotropic actions in skin structures. It is known that the phenomena of microcapillary dilation and increased permeability figure among the early cutaneous responses upon UV exposure.

Roles of VEGF and $PGE_2$ in the conformational changes of skin microcapillaries: The reactions of skin microcapillary dilation and hyperpermeability are characteristic of an excessive UV exposure and lead to the inflammation of the skin (Matsumura Y, Ananthaswamy H N. Toxicol Appl Pharmacol. 2004 Mar. 15; 195(3):298-308). Microcapillary integrity is influenced by biochemical mediators such as cytokines and other specific growth factors found in the skin. Among these, the pro-inflammatory prostaglandin $E_2$ ($PGE_2$) plays a central role in the skin's response to stress as its expression is readily triggered by inflammatory stimuli (Kabashima K, Miyachi Y. Journal of Dermatological Science. 2004; 34:177-184; Lee J L, Mukhtar H, Bickers D R, Kopelovich L, Altar M. Tox Appli Pharmacol. 2003; (192):294-306; Bachelor M A, Bowden G T. Seminars in Cancer Biology. 2004; 14:131-138). The expression of $PGE_2$ is upregulated in skin following exposure to UV (Hruza L L, Pentland A P. J Invest Dermatol. 1993 January; 100(1):35S-41S) whereby it acts upon specific cell receptors and mediates microcapillary dilation (Lee J L, Mukhtar H, Bickers D R, Kopelovich L, Altar M. Tox Appli Pharmacol. 2003; (192):294-306). The UV-induced increase in $PGE_2$ may be achieved through multiple signal transduction pathways (Ashida M, Bito T, Budiyanto A, Ichihashi M, Ueda M. Experimental Dermatology. 2003; 12:445-452). Furthermore, dilated microcapillaries are also more susceptible to the leakage of leukocytes into the ECM where they can release pro-inflammatory cytokines, growth factors and degradation enzymes. This can be demonstrated in the inflammatory skin condition rosacea, which is characterized by the presence of dilated vessels (Van Zuuren E, Graber M, Hollis S, Chaudhry M, Gupta A, Gover M. Cochrane Database Syst Rev. 2005 Jul. 20; (3):CD003262) and a collapsed EGM structure (Crawford G H, Pelle M T, James W D. J AM Acad Dermatol. 2004 September; 51 (3):327-41).

The Vascular Endothelial Growth Factor (VEGF) is also a factor known to be induced in keratinocytes and fibroblasts by a specific range of effectors such as tissue hypoxia (Detmar M, Brown L F, Berse B. Jackman R W, Elicker B M, Dvorak H F, Claffey K P. J Invest Dermatol. 1997 March; 108(3):263-8.), pro-inflammatory cytokines (Trompezinski S, Berthier-Vergnes O, Denis A, Schmitt D, Viac J. Exp Dermatol. 2004 February; 13(2):98-105), nitric oxide (Frank et al., 1999), toxins (Deasi A, Lankford H A, Warren J S. Inflammation. 2000 February; 24(1):1-9) and upon exposure to UV. VEGF is a regulator of angiogenesis (the formation of new blood vessels) in inflammatory conditions (Detmar M, Brown L F, Schon M P, Elicker B M, Velasco P, Richard L, Fukurama D, Monsky W, Claffey K P, Jain R K. J Invest Dermatol. 1998 July; 111(1):1-6). For instance, the expression of this growth factor has been shown to be upregulated in psoriasis (Detmar, 1994) as well as in rosacea (Lachgar S, Charveron M, Gall Y, Bonafe J L. Dermatology. 1999; 199 Suppl 1:25-7). Keratinocytes represent an important source of VEGF (Ballaun C, Weninger W, Uthman A, Weich H, Tschachler. J Invest Dermatol. 1995 January; 104(1):7-10). VEGF expression in these cells may be induced via both UVA and UVB and it has been suggested that this induction mechanism differs according to the specific type of stimuli (Gille J, Reisinger K, Asbe-Volikopf A, Hardt-Weinelt K, Kaufmann R. J Invest Dermatol. 2000 July; 115(1):30-6; Kosmadaki M G, Yaar M, Arble B L, Gilchrest B A. FASEB J. 2003 March; 17(3):466-8; Longuet-Perret I, Schmitt D, Viac J. Br J. Dermatol. 1998 February; 138(2):221-4). VEGF affects a host of parameters of skin microvasculature; the most prominent being the increase in permeability of microcapillaries (Dvorak H F, Brown L F, Dvorak A M. Am J. Pathol. 1995 May; 146(5):1029-39). It has been postulated that VEGF (first known as the Vascular Permeability Factor) induces microcapillary hyperpermeability through the loosening of endothelial cell-cell interaction creating microbreaches through which leukocytes (neutrophils) and plasma exudate (Harhaj N S, Antonetti D A. Int J Biochem Cell Biol. 2004 July; 36(7):1206-1237).

Additionally, VEGF secretion by the fibroblasts has been shown not only to be upregulated by UV, but also by $PGE_2$ itself (Trompezinski S, Pernet I, Schmitt D, Viae J. Inflamm Res. 2001; (50):422-427). The autocrine/paracrine effect of $PGE_2$ on VEGF secretion by skin cells exemplifies the complex cell-cell communication which exists under stressful conditions. With the aging process, positive regulation of $PGE_2$ on VEGF secretion becomes even more strategic as UV-induced $PGE_2$ production in the skin increases as one ages (Seo J Y, Kim E K, Lee S H, Park K C, Kim K H, Eun H C, Chung J H. Mechanisms of Ageing and Development. 2003; (124): 903-910). This observation further illustrates the cross-talks that occur between the biochemical pathways involved in both chronological aging and actinic aging. A synergistic superimposition of these two aging modes would accelerate the loss of integrity of skin microcapillaries (dilation and hyperpermeability) and exacerbate leukocyte efflux.

Neutrophils (a subset of leukocytes also referred to as polymorphonuclear cells) efflux towards the ECM as a result of microcapillary dilation and hyperpermeability. Evolving scientific knowledge provides increasing support for the importance of dermo-epidermal infiltrating neutrophils as effectors in the process of photo-damage. Neutrophils represent important cellular sources of not only elastase but also of other known ECM-degradation enzymes such as the metalloproteinases (MMP-1, MMP-8 and MMP-9; Rijken F, Kiekens R C M, Bruijnzeel P L B. British Journal Dermatology. 2005 February; 152(2):321-8). Most of the emphasis within the scientific community focused around MMPs and their action in causing the breakdown of collagen fibers and other ECM macromolecules. However, the action of a specific catabolic enzyme, elastase, may also impose significant consequences to the integrity of the ECM and its components. Elastase targets specific molecular substrates (elastin fibers) that may differ from those attacked by MMP (mainly collagen fibers), however, the outcome is similar and translates into the comparable disorganisation of the skin ECM.

Human leukocyte elastase (HLE), a broad spectrum serine protease of 30 kDa, is a specific elastolytic enzyme that is involved in the turnover of elastic fibers and the remodelling of the ECM. Elastin fibers are mostly responsible for the resiliency of the skin's ECM. Even though elastin fibers represent less than 2% of the total dry weight of the skin (in comparison, collagen fibers comprise more than 70% of total skin dry weight), they intermingle in functional interactions with other fibrillar macromolecules and provide the viscoelastic properties required for normal skin functions.

Released from a signal source, cytokines initiate the efflux of neutrophils toward the ECM, seemingly mimicking an inflammatory reaction. Neutrophils gain access to the signal source by migrating through the connective tissue thereby destroying encountered fibrillar components. Once in the connective tissue, neutrophils cells actively continue the secretion of degradation enzymes thereby continuing their mission by breaking down elastic fibers of the ECM. Excessive proteolytic activity of proteolytic enzymes such as MMPs and neutrophil elastase is known to be associated with structural alteration of the tridimensional organization of the ECM. Ultimately, these histological modification deleterious changes will translate into macroscopic symptoms degeneration deterioration and become visible in the form of fine lines and wrinkles; hallmarks of skin aging.

The importance of elastic fibers for the maintenance of skin resiliency and elasticity is well exemplified in the many skin disorders in which the integrity of elastin network is affected (Lewis K G, Bercovitch L, Dill S W, Robinson-Bostom L. J Am Acad Dermatol. 2004 July; 51(1):1-21; Lewis K G, Bercovitch L, Dill S W, Robinson-Bostom L. J Am Acad Dermatol. 2004 August; 51(2): 165-85).

The integrity of the ECM and its dynamic interactions with skin cells is of primary importance in tissue repair (Midwood K S, Williams L V, Schwarzbauer J E. Int J Biochem Cell Biol. 2004 Juhn; 36(6):1031-7).

A relationship has been established between UV exposure, up-regulation of VEGF, exudation of elastase-producing neutrophils in the skin, disorganisation of the elastin compartment of the ECM and the appearance photo-damage (Yano K, Kadoya K, Kajiya K, Hong Y K, Detmar M. Br J. Dermatol. 2005 January; 152(1):115-21). The same research group (Yano K, Kajiya K, Detmar M. A novel mechanism of cutaneous photo-damage mediated by angiogenesis and inhibitory effects of *chlorella* extract on UV-induced angiogenesis. 23rd IFSCC Congress. 2004; 46-51) has shown that a *Chlorella* extract (a green algae extract) increases trombospondin-1 (TSP-1) expression in UVB irradiated keratinocytes and prevents UVB-induced predominant expression of VEGF against TSP-1 in vitro.

Cellular and molecular mechanisms triggered by UV and leading to the appearance of clinical signs of actinic aging may reflect a confused inflammatory and repair elicited response of the skin in reaction to environmental aggressions.

Thus, some pathologies are accompanied by a chronic inflammatory state of the connective tissue in which the balance between the destruction, repair and resolution phases is upset which leads to defective reconstruction of the lesioned tissue.

With this aim, the inventors have studied the action of various polysaccharide compositions. It is known that specific polysaccharide compositions, such as glycosaminoglycans, participate in the composition of the proteoglycans present at the cell/extracellular matrix interface, and play a role in regulating cell functions. It is also known that glycosaminoglycans in a soluble form, for example heparin or dextran derivatives, can modify cell functions via their interaction with various components of the ECM.

Ferrao and Mason (Biochem. Biophys. Acta. 1180, 225-230, (1993)) have studied the action of various polysaccharides on human dermal fibroblast proliferation, and indicated that at concentrations of about 100 µg/ml, heparin, heparan sulfate, pentosan polysulfate and a fucoidan inhibit this proliferation, whereas chondroitin sulfate, dermatan sulfate and hyaluronate have no effect. It is indicated that the inhibitory effect on proliferation leads to a stimulation of type I collagen synthesis. Conversely, an inhibition of collagen I synthesis is observed when the polysaccharides are added to cultures which have reached confluence.

Berteau and Mulloy (Glycobiology 13(6): 29R-40R, 2003) have made a review on fucans, wherein it is said that, like heparin, they have anti-proliferative effects on vascular smooth muscle cells and on fibroblasts, in addition to an anti-coagulant effect. Nothing is disclosed on the activity of fucans on VEGF or on inflammation mediators, except for TNF-alpha.

Matsumoto et al. (Clin. Exp. Immunol 136(3): 432-439, 2004) showed that oral ingestion of fucans from *Cladosiphon okamuranus* Tokida (0.05% w/w with food) inhibits the release of Interferon gamma and IL-6 by colonic lamina propria cells. They propose fucans as dietary supplement for treating patients with inflammatory bowel disease.

Zhang et al. (Zhang Q, Li N. Qi H Xu Z. Li Z Phytother Res. 2005 January; 19(1):50-3) reported that elevated urinary protein excretion and plasma creatinine due to the induction of Heymann nephritis were significantly reduced by fucoidan oral administration at doses of 100 and 200 mg/kg, daily. The renoprotective effect of fucoidan on active Heymann nephritis is a good indication of its bioavailability after oral administration.

Li et al (Li N., Zhang Q, Song J. Food Chem. Toxicol. 2005 March; 43(3):421-6) investigate the acute and subchronic (6 months) toxicity of fucoidan extracted from *Laminaria japonica* in Wistar rats. Fucoidans did not show significant toxicological changes when 300 mg/kg body weight per day of fucoidan was orally administered. However, the clotting time was significantly prolonged when the dose was increased to 900 and 2500 mg/kg body weight per day. Besides this, no other signs of toxicity were observed. Based on these results, it can be concluded that no adverse effect level of fucoidan from *L. japonica* is observed at or below 300 mg/kg body weight per day.

Granert et al. (J. Clin. Invest. 93: 929-936, 1994) disclose that fucans, administered i.v. (10 mg/Kg body weight) reduce the accumulation of leukocytes and plasma proteins in the CSF of rabbits intrathecally challenged with pneumococcal antigen. They also show that fucans inhibit leukocyte recruitment into an inflamed tissue site (rabbit skin) thus suggesting that fucans may be effective when administered in situ or at a distance from the inflamed site.

Preobrazhenskaya et al. (Biochem. Mol. Biol. Int. 43(2): 443-451, 1997) show that neutrophil recruitment into an inflammatory site (rat peritoneum) is reduced by fucans administered i.v. (0.8 mg). The anti-extravasation effect is quite remarkable but has a short duration.

One of the drawbacks of the use of fucans and galactans is their cytotoxicity. Stevan et al (J. Submicrosc. Cytol. Pathol. 33(7): 477-484, 2001) show that fucans, particularly, at a sulfate/sugar ratio of 1.9 and concentration of 2.5 microgram/mL cause toxicity in HeLa cells, as seen from the atypical nuclei, altered cell morphology and impaired cell division.

There is therefore a need to improve fucans compositions to increase their efficacy and decrease their toxicity.

The present invention seeks to meet these needs and other needs.

The present description refers to a number of documents, the content of which is herein incorporated by reference in their entirety.

SUMMARY OF THE INVENTION

More specifically, in accordance with the present invention, there is provided a use of an anti-inflammatory polysaccharides composition comprising fucans and galactans to inhibit the release of one or more of IL-8, PGE2 and VEGF by a cell activated during an inflammatory process.

In accordance with another aspect of the present invention, there is provided a use of an anti-inflammatory polysaccharides composition comprising fucans and galactans in the manufacture of a medicament to inhibit the release of one or more of IL-8, PGE2 and VEGF by a cell activated during an inflammatory process.

In accordance with specific embodiments of these uses, the release of IL-8, PGE2 and VEGF is from epithelial cells. According to other specific embodiments, the fucans increase the inhibition of inflammation, and reduce the cytotoxicity of the galactans. According to still other specific embodiments, the galactans are obtained from red algae. According to still other specific embodiments, the red algae are *Asparagopsis armata*. According to still other specific embodiments, the fucans are obtained from brown algae. According to still other specific embodiments, the brown algae are *Ascophyllum nodosum*. According to still other specific embodiments, the galactans have an average molecular weight higher than about 100 kDa. According to still other specific embodiments, the galactans have an average molecular weight of about 350 kDa. According to still other specific embodiments, the galactans have a galactose content of about 37% of dry weight of the galactans. According to still other specific embodiments, the galactans have an uronic acid content of about 3% of dry weight of the galactans. According to still other specific embodiments, the galactans have a sulfate content of about 27% of dry weight of the galactans. According to still other specific embodiments, the fucans have an average molecular weight ranging from about 0.1 kDa to about 100 kDa. According to still other specific embodiments, the fucans have an average molecular weight ranging from about 5 kDa to about 25 kDa. According to still other specific embodiments, the fucans have a fucose content of about 20-35% of dry weight of the fucans. According to still other specific embodiments, the fucans have an uronic acid content of about 10 to about 29% of dry weight of the fucans. According to still other specific embodiments, the fucans have a sulfate content of about 15 to about 25% of dry weight of the fucans. According to still other specific embodiments, the ratio fucans/galactans present in the composition is between about 2.5/1 (w/w) to about 40/1 (w/w). According to still other specific embodiments, the fucans and the galactans are present a ratio of about 10 fucans/1 galactans (w/w) in the composition. According to still other specific embodiments, the galactans comprise native galactans. According to still other specific embodiments, the fucans comprise native fucans. According to still other specific embodiments, the fucans comprise depolymerized fucans. According to still other specific embodiments, the fucans comprise demineralized fucans. According to still other specific embodiments, the galactans comprise demineralized galactans. According to still. other specific embodiments, the use is a topical use. According to still other specific embodiments, the use is to alleviate or improve skin disorders or conditions caused by UV exposure, chemical stress or aggression from pollutants, exfoliating agents or skin irritants. According to still other specific embodiments, the use is to prevent skin disorders or conditions caused by UV exposure, chemical stress or aggression from pollutants, exfoliating agents or skin irritants.

In accordance with another aspect of the present invention, there is provided an anti-inflammatory composition comprising a ratio of brown algae fucans/red algae galactans of between about 2.5/1 (w/w) to about 40/1 (w/w), the galactans having a molecular weight higher than about 100 kDa, and the fucans having a molecular weight between about 0.1 kDa and 100 kDa. According to specific embodiments, the galactans have an average molecular weight of about 350 kDa. According to other specific embodiments, the galactans have a galactose content of about 37% of dry weight of the galactans. According to still other specific embodiments, the galactans have an uronic acid content of about 3% of dry weight of the galactans. According to still other specific embodiments, the galactans have a sulfate content of about 27% of dry weight of the galactans. According to still other specific embodiments, the fucans have an average molecular weight ranging from about 5 kDa to about 25 kDa. According to still other specific embodiments, the fucans have a fucose content of about 20-35% of dry weight of the fucans. According to still other specific embodiments, the fucans have an uronic acid content of about 10 to about 29% of dry weight of the fucans. According to still other specific embodiments, the fucans have a sulfate content of about 15 to about 25% of dry weight of the fucans. According to still other specific embodiments, the ratio of brown algae fucans/red algae galactans being of 10/1. According to still other specific embodiments, the galactans having a molecular weight of about 350 kDa, and the fucans having a molecular weight between about 15 kDa and 25 kDa. According to still other specific embodiments, the brown algae is *Ascophyllum nodosum*. According to still other specific embodiments, the red algae is *Asparagopsis armata*. According to still other specific embodiments, the galactans comprise native galactans. According to still other specific embodiments, the fucans comprise native fucans. According to still other specific embodiments, the fucans comprise depolymerized fucans. According to still other specific embodiments, the fucans comprise demineralized fucans. According to still other specific embodiments, the galactans comprise demineralized galactans. According to still other specific embodiments, the composition is a topical composition. According to still other specific embodiments, the composition is a cosmetic composition.

In accordance with another aspect of the present invention, there is provided a method of inhibiting the release of one or more of IL-8, PGE2 and VEGF by a cell activated during an inflammatory process comprising administering to a subject a polysaccharides composition comprising fucans and galactans. According to specific embodiments of the method, the polysaccharides composition is topically administered to the subject. According to other specific embodiments of the method, the subject is a human affected by skin disorders or conditions caused by UV exposure, chemical stress or aggression from pollutants, exfoliating agents or skin irritants.

As used herein the term "fucans" refers to polysaccharides comprising sulfated fucose and uronic acid, wherein the polysaccharides have antiinflammatory and anti-extravasation activities. Without being so limited, fucans derived from Laminariales, Chordariales, Fucales marine algae including *Kjellmaniella crassifolia, Laminaria japonica, Kjellmaniella, Fucus, Nemacystus, Cladosiphon okamuranus, Undaria, Undaria pinnatifida* (Wakame Mekabu), *Ecklonia kurome, Eisenia, Ecklonia,* Giant kelp, *Lessonia nigrescence Gelidiun amansii, Gracilaria, Pteroclavia capillacae* and *Ascophyllum nodosum* along with those derived from Echinodermata, sea cucumber, Echnoidea and Asterozoa are suitable for uses and methods of the present invention. Fucans of the present invention are exemplified herein by fucans derived from the brown algae *Ascophyllum nodosum*.

As used herein the term "galactans" refers to polysaccharides comprising sulfated beta-D-galactose, xylose and uronic acid. Without being so limited, Rhodomelaceae, Corallinaceae, Gracilariales, Ceramiales, Gigartinales marine algae, including *Asparagopsis armata, Bostrychia maontanei, Corallina* species, *Polysiphonia lanosa, Gracilaria* species, *Acanthophora spicifer, Georgiella confluens, Laurencia coronopus, Porphyra haitanensis, Botryocladia occidentalis, Chondrus ascellatus, Gymnogongrus tolurus, Phacelocarpus peperocarpos, Sargassum kjellmanianum,* contain galactans suitable for uses and methods of the present invention. The galactans of the present invention are exemplified herein by galactans derived from the red algae *Asparagopsis armata*.

The term "about" when used in relation to ranges apply to both ends of the range. It is used to reflect the relative precision of the equipment and process used to obtain and to characterize the compositions of the present invention.

The articles "a," "an" and "the" are used herein to refer to one or to more than one (i.e., to at least one) of the grammatical object of the article. The term "including" and "comprising" are used herein to mean, and re used interchangeably with, the phrases "including but not limited to" and "comprising but not limited to".

The term "such as" is used herein to mean, and is used interchangeably with, the phrase "such as but not limited to".

As used herein the term "subject" is meant to refer to any mammal including human, mice, rat, dog, cat, pig, cow, monkey, horse, etc. In a particular embodiment, it refers to a human.

As used herein the term "anti-inflammatory" with regards to the polysaccharides compositions of the present invention relate to their ability to inhibit VEGF and/or IL-8 and/or PGE2.

Applications of the polysaccharides compositions of the present invention include topically applicable cosmetic compositions. Non-limitative examples of such topically applicable compositions include skin care cream, cleansing cream, skin care lotion, skin care gel, skin care foam, sun care composition, make-up removal cream, make-up removal lotion, foundation cream, liquid foundation, bath and shower preparation, deodorant composition, antiperspirant composition, shaving products composition, after-shave gel or lotion, beauty aids composition, depilatory cream, soap composition, hand cleaner composition, cleansing bar, baby care, hair care, shampoo, setting lotion, treatment lotion, hair cream, hair gel, coloring composition, restructuring composition, permanent composition, anti-hair loss composition, or any other composition which is adapted for the use in a topical cosmetic regimen.

Polysaccharides compositions of the present invention may comprise at least one additional active ingredient. Without being so limited, such additional active ingredient may modulate at least one of cell differentiation, cell metabolic activity, cell structure, cell proliferation, extracellular processes and pigmentation. Without being so limited, the polysaccharides compositions of the present invention may further comprise at least one of an anesthesic agent, anti-acne agent, anti-aging agent, antibacterial agent, anticellulite agent, antifungal agent, anti-inflammatory agent, anti-irritant agent, antioxidant agent, antiparasitic agent, antipollution agent, antipruritic agent, anti-rosacea agent, anti-seborrhea agent, anti-stress agent, anti-telangiectasia agent, antiviral agent, anti-wrinkle agent, baby care agent, bath and body agent, calming agent, cleansing agent, collagen synthesis agent, elastase inhibitory agent, exfoliant agent, facial peeling agent, firming agent, foot care agent, free radical scavenging agent, immune function modulator agent, keratolytic agent, lift agent, make-up remover agent, melanogenesis stimulator agent, matrix metalloproteinase inhibitory agent, moisturizing agent, oil absorbent agent, osmoregulator agent, anti-photoaging agent, protecting agent, rejuvenating agent, regenerating agent, restructuring agent, sensitive skin agent, shaving product agent, skin defense enhancer agent, skin clarifier agent, skin repair agent, slimming agent, smoothing agent, softening agent, soothing agent, sun care agent, sunless tanning agent, tensing agents and whitening agent, or any other agent adapted for use in a cosmetic regimen that comprises topical application of said cosmetic composition, and which complements or supplements the effect of the polysaccharides of the present invention.

Without being so limited, agents that modulate cell differentiation or proliferation include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin D and its derivatives (cholecalciferol, ergocalciferol, 25-hydroxycholecalciferol), growth factors and estradiol derivatives.

Without being so limited, anaesthesics include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include lidocaine chlorhydrate and its derivatives.

Without being so limited anti-acne agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include benzoyl peroxide, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), salicylic acid, sulfur, sulfurated lime, alcohol and acetone.

Without being so limited, anti-aging/anti-wrinkle agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include hyaluronic acid, sodium-2-pyrrolidone carboxylate, glycosaminoglycans, kinetin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), epidermal growth factor, ceramide, ethylbisiminomethylgualacol manganese chloride, glycation inhibitors, chrysanthellum *indicum* extract and aphanizomenon flos aquae extract.

Without being so limited, antibacterial agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *eucalyptus* extract, clindamycin phosphate, cavacrol, erythromycin and antibiotics belonging to the group of tetracyclines.

Without being so limited, antifungal agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include. econazole, ketoconazole, miconazole, amphotericin B, terbinafine and octopirox.

Without being so limited, anti-inflammatory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, vitamin E and its derivatives (α-tocopherol, δ-tocopherol, γ-tocopherol), chamomile oil, *gingko biloba* oil and *camellia sinensis* extract.

Without being so limited, anti-irritant/soothing/smoothing/calming agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include allantoin, *camellia sinensis* extract, lavender oil, *aloe vera*, linden extract, epilobium angustifolium extract, chysanthellum *indicum* extract, cola nitida extract and alteromonas ferment extract.

Without being so limited, antioxidant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include furfuryladenine, panthenol, lipoic acid, ubiquinone, niacinamide, melatonin, catalase, glutathione, superoxide dismutase, polyphenols, cysteine, allantoin, kinetin, vitamin C and its derivatives (ascorbyl palmitate, magnesium ascorbyl phosphate, sodium ascorbyl phosphate), vitamin E and its derivatives (α-tocopherol, δ-tocopherol, γ-tocopherol), grape seed extract and *camellia sinensis* extract.

Without being so limited, antipruritic agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include thenaldine, trimeprazine, cyproheptadine.

Without being so limited, anti-rosacea/anti-telangiectasia agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include metronidazole, vasoconstrictors, benzoyl peroxide, azelaic acid, sulphur, soy proteins and glycosaminoglycans.

Without being so limited, anti-seborrhea agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include progesterone derivatives, isoleutrol and hinokitiol.

Without being so limited, sensitive skin agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rose oil and jasmine oil.

Without being so limited, cleansing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include ammonium lauryl sulfate, ammonium laureth sulfate, cocamide MEA, triethanolamine lauryl sulfate, sodium stearate and nettle leaf extract.

Without being so limited, collagen synthesis agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), vitamin C and its derivatives (ascorbyl palmitate, magnesium ascorbyl phosphate, sodium ascorbyl phosphate), growth factors and its derivatives.

Without being so limited, exfoliant agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include alpha/beta hydroxy acids, salicylic acid, glycolic acid, lactic acid, citrus acid and walnut shell powder.

Without being so limited, facial peeling agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include glycolic acid, lactic acid, trichloroacetic acid and phenol.

Without being so limited, firming/tensing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dimethylaminoethanol, neuro-cosmetic actives (Botox™-like), chitosan, *arnica* extract, fennel-sweet oil and *papaya* extract.

Without being so limited, free radical scavenging/antipollution/anti-stress agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include grape seed extract, alpha-tocopherol and the esters thereof, superoxide dismutase, some chelating agents of metals, vitamin C and its derivatives (ascorbyl palmitate, magnesium ascorbyl phosphate, sodium ascorbyl phosphate).

Without being so limited, hair care agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-D-glucosamine, poly-N-acetyl-D-glucosamine, stearalkonium chloride and triethanolamine lauryl sulfate.

Without being so limited, matrix metalloproteinase inhibitory agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include *camellia sinensis* extract, polyphenols, spatholobi caulis extract, *euonymus alatus* extract, rhizoma notopterygii extract, quercetin, glycosaminoglycans, polymethoxy flavonoid, N-acetyl-cysteine, 2-furildioxime, isoflavone, vitamin C and its derivatives (ascorbyl palmitate, magnesium ascorbyl phosphate, sodium ascorbyl phosphate), retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester) and hydroxamate derivatives.

Without being so limited, moisturizing agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include cucumber extract, sodium-2-pyrrolidone carboxylate, sodium PCA, sodium hyaluronate, chitin and its derivatives, alpha hydroxy acids, hyaluronic acid and hydrolysed wheat protein.

Without being so limited, osmoregulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include mannitol, dulcitol and betaine.

Without being so limited, protecting agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include poly-N-acetyl-D-glucosamine, poly-D-glucosamine, alkyloamides, chitosan, chrysanthellum *indicum* extract, *camellia sinensis* extract and alteromonas ferment extract.

Without being so limited, rejuvenating agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include rosemary extract, rosewood extract, geranium extract and vitamin E and its derivatives (α-tocopherol, δ-tocopherol, γ-tocopherol).

Without being so limited, skin repair agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), allantoin, *eucalyptus* extract, lavender oil, rose oil and activators of collagen synthesis and activators of components of the skin's extracellular matrix.

Without being so limited, slimming/anticellulite agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include chrysanthellum *indicum* extract, dihydromyricetin, theobromine, theophylline, aminophylline, caffeine, isopropylarterenol hydrochloride, epinephrine, α-MSH agonists, adenylate cyclase activators and phosphodiesterase inhibitors.

Without being so limited, sun care/photo aging agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include PABA (p-aminobenzoic acid) and derivatives, gluconolactone, salicylates, cinnamates, benzophenones, dibenzoylmethanes, oxybenzone, vitamin E and its derivatives (α-tocopherol, δ-tocopherol, γ-tocopherol), ethylbisiminomethylgualacol manganese chloride, glycosaminoglycans, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), titanium dioxide, octyl methoxycinnamate, benzophenone, octyl salicylate, epilobium angustifolium extract, *rumex occidentalis* extract, chrysanthellum *indicum* extract, *camellia sinensis* extract and alteromonas ferment extract.

Without being so limited, sunless tanning/melanogenesis stimulator agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include dihydroxyacetone, α-MSH agonists, adenylate cyclase activators and phosphodiesterase inhibitors.

Without being so limited, toning agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include nettle extract, orange blossom extract, rosewood extract and witch hazel extract.

Without being so limited, whitening/pigmentation agents include plant extracts, algae extracts, fruit extracts, vegetable extracts, leguminous plant extracts, ferments, proteolytic hydrolysates, peptides, yeast extracts and its derivatives, microorganism extracts, animal derivative extracts and synthetic compounds. More particularly, such agents include arbutin, azealeic acid, vitamin C and its derivatives (ascorbyl palmitate, magnesium ascorbyl phosphate, sodium ascorbyl phosphate), hydroquinone, N-acetyl-4-S-cysteanimylphenol, kojic acid, melanostat (melanostatine), tretinoin, retinoic acid and its derivatives (retinol, retinaldehyde, retinyl palmitate, trans-retinoic acid, 13-cis retinoic acid, 9-cis retinoic acid, retinoyl glucuronoides, tretinoin, isotretinoin, etretinate, acitretine, tazarotene, adapalene, β-carotene, retinyl ester), *ruminex occidentalis* extract, licorice, mulberry, arctostaphylos uva-ursi (bearberry), tyrosinase inhibitors, melanosome-transfer inhibitors and melanin scavengers.

The polysaccharides composition of the present invention may be formulated so as to provide for a specifically controlled delivery system. Non-limitative examples of such delivery systems include slow delivery system, rapid delivery system, immediate delivery system, delayed delivery system, zero-order delivery system and dual or multiple speed delivery system. Such controlled delivery systems may be achieved with specific formulations including chemical delivery systems, multiple emulsions, microemulsions, nanoemulsions, encapsulations such as liposomes, microspheres, nanospheres, microsponges, beads and cyclodextrins, polymeric matrices, polymeric cosmetic conjugates, oil body/oleosin, oil-soluble molecular film, skin patches, unit dosages.

The polysaccharides compositions of the present invention may be formulated into a cosmetically acceptable vehicle including a solution, dispersion, lotion, serum, microgranulate dispersion, vesicular ionic or non-ionic dispersion, alcoholic or hydro-alcoholic aqueous solution, cream, gel, oil-in-water or water-in-oil emulsion, foam, aerosol, solid or paste.

The polysaccharides compositions of the present invention may further comprise additional excipients such as buffer agent, carrier agent, chelating agent, conditioner agent, coloring agent, detackifier agent, emollient agent, emulsifier agent, film former agent, foaming agent, humectant agent, lactylate agent, lipophilic agent, lubricant agent, neutralizer agent, oil agent, opacifier agent, preservative agent, solubilizer agent, solvent agent, stabilizer agent, surfactant agent, thickener agent, viscosity agent, water absorbent agent and wetting agent.

Without being so limited, buffer agents are salts of bases/acids, compatible with the nature of the skin and with its pH. Sodium acetate is an example of a frequently used buffer agent.

Without being so limited, carrier agents are ingredients capable of aiding the application of the active ingredient. Isohexadecane is an example of a frequently used carrier.

Without being so limited, chelating agents are ingredients capable of binding mono and divalent cations, such as tetrasodium EDTA and disodium EDTA.

Without being so limited, conditioner agents are ingredients with lubricating action and hydrating effect, such as cetrimonium chloride, dicetyldimonium chloride, trideceth-I2, quaternium-Z7, quaternium-I8, polyquaternium-10, behentrimonium methosulfate, cetearyl alcohol, stearamidopropyl dimethylamine, trimethylsilylamodimethicone, isolaureth-6, octoxynol-4, dimethicone, dimethiconol, cyclopentasiloxane, pareth-7, pareth-9, linoleic acid and glycerin.

Without being so limited, detackifier agents are ingredients capable of adsorbing onto tacky materials and reduce their tendency to adhere, such as cyclopentasiloxane, dimethicone and vinyl dimethicone, phenyl trimethicone, isopropyl esters, isostearate esters, dimethyl sebacate and dipropyl sebacate.

Without being so limited, emollient agents are ingredients with lubricating action and hydrating effect, such as isopropyl palmitate, sunflower seed oil, mineral oil, stearyl stearate, isopropyl myristate, lanolin, caprylic, capric triglyceride, cyclopentasiloxane, dimethicone, vinyl dimethicone, bisphenylpropyl dimethicone, alkyl dimethicone, sorbitan stearate, sucrose distearate, myristyl alcohol, myristyl lactate, cetyl acetate, dicaprylyl ether, floraester-20, maleated soybean oil, cyclomethicone, shea butter, hydrogenated coconut oil, isopropyl palmitate, diisostearoyl trimethylolpropane siloxy silicate and alkyl benzoate.

Without being so limited, emulsifier agents are ingredients capable of preventing the separation of immiscible substances in an emulsion, of helping to distribute evenly one substance in another, of improving texture, homogeneity, consistency and stability, such as cetearyl alcohol, glyceryl stearate, alkyl acrylate crosspolymer, stearic acid, emulsifying wax, sorbitan oleate, sorbitan stearate, polysorbate, polyethylene glycopolysorbate, triethanolamine, cyclopentasiloxane, dimethicone copolyol, PEG-30 dipolyhydroxystearate, sucrose distearate, PEG-100 stearate, sodium dioctylsulfosuccinate, polyacrylamide, isoparaffin, laureth-7, cetyl phosphate, DEA cetyl phosphate, glycol stearate, stearyl alcohol, cetyl alcohol, behentrimonium methosulfate and ceteareth-2.

Without being so limited, film former agents are ingredients capable of forming a dimensionally stable and continuous film to minimize the formula tackiness, such as wheat protein, eicosene copolymer, perfluoromethylisopropyl ether, diisostearoyl trimethylolpropane siloxy silicate, trimethylsiloxysilicate, dimethicone, vinyl dimethicone and cyclopentasiloxane.

Without being so limited, foaming agents are ingredients capable of regulating the amount of air in a product, such as lauramide DEA and cocamide MEA, disodium laureth sulfosuccinate, disodium N-octadecyl sulfosuccinamate, ammonium lauryl sulphate, triethanolamine lauryl sulfate, sodium lauryl sulphate and sodium 2-ethylhexylsulfate.

Without being so limited, humectant agents are ingredients capable of maintaining constant humidity and retaining moisture, such as glycerine, PEG-8, butylene glycol and propylene glycol.

Without being so limited, lubricant agents are ingredients capable of adding slipperiness and reducing friction to improve application, such as dimethicone and dimethicone copolyol.

Without being so limited, neutralizer agents are ingredients capable of changing the acid-alkaline balance, such as triethanolamine and sodium hydroxide.

Without being so limited, opacifier agents are ingredients capable of changing the look of a clear or translucent product to a creamier or pearlier one, such as glyceryl stearate and PEG-100 stearate.

Without being so limited, preservative agents are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben.

Without being so limited, solubilizer agents are ingredients capable of allowing incompatible ingredients to become part of a homogeneous solution, such as polysorbate, ceteareth, steareth and PEG.

Without being so limited, stabilizer agents are ingredients capable of maintaining physical and chemical properties during and after processing, preventing or limiting changes in the physical properties of a substance during product life, such as polyethylene, sodium chloride, stearyl alcohol, xanthan gum, tetrasodium EDTA and dimethicone copolyol.

Without being so limited, surfactant agents are ingredients capable of reducing surface tension when dissolved in water or a water solution, reducing interfacial tension between two liquids or between a liquid and a solid, such as sodium dioctylsulfosuccinate, octoxynol-40, isolaureth-6, ammonium lauryl sulfate, lauryl alcohol, lauramide DEA and cocoamidopropyl betaine.

Without being so limited, thickener agents are ingredients capable of absorbing water to impart body, improve the consistency or texture, and stabilize an emulsion, such as stearic acid, magnesium aluminum silicate, carbomer, alkyl acrylate crosspolymer, polyacrylamide, isoparaffin, laureth-7, cetyl alcohol, xanthan gum, alkyl dimethicone, hydroxyethylcellulose, glyceryl stearate, pentaerythrityl tetrastearate, stearyl alcohol and polyquaternium-10.

Without being so limited, viscosity agents are ingredients capable of controlling the degree of fluidity and the internal resistance to flow exhibited by a fluid, such as magnesium aluminum silicate, caprylyl glycol and myristyl alcohol.

Without being so limited, water absorbent agents are ingredients capable of absorbing the product's water to maintain the moisture, such as carboxyvinyl polymer, acrylic copolymer, polyacrylamide, polysaccharides, natural gum, clay, modified clay, metallic salt and fatty acid.

Without being so limited, wetting agents are ingredients capable of reducing the surface tension of the water for better penetration or spread over the surface, such as caprylate, caprylyl glycol, glyceryl caprate, polyglyceryl-2 caprate, polyglyceryl-6, polyglyceryl-3 laurate and TEA-laureth sulfate.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Preparation of Fucans

Figure 1:
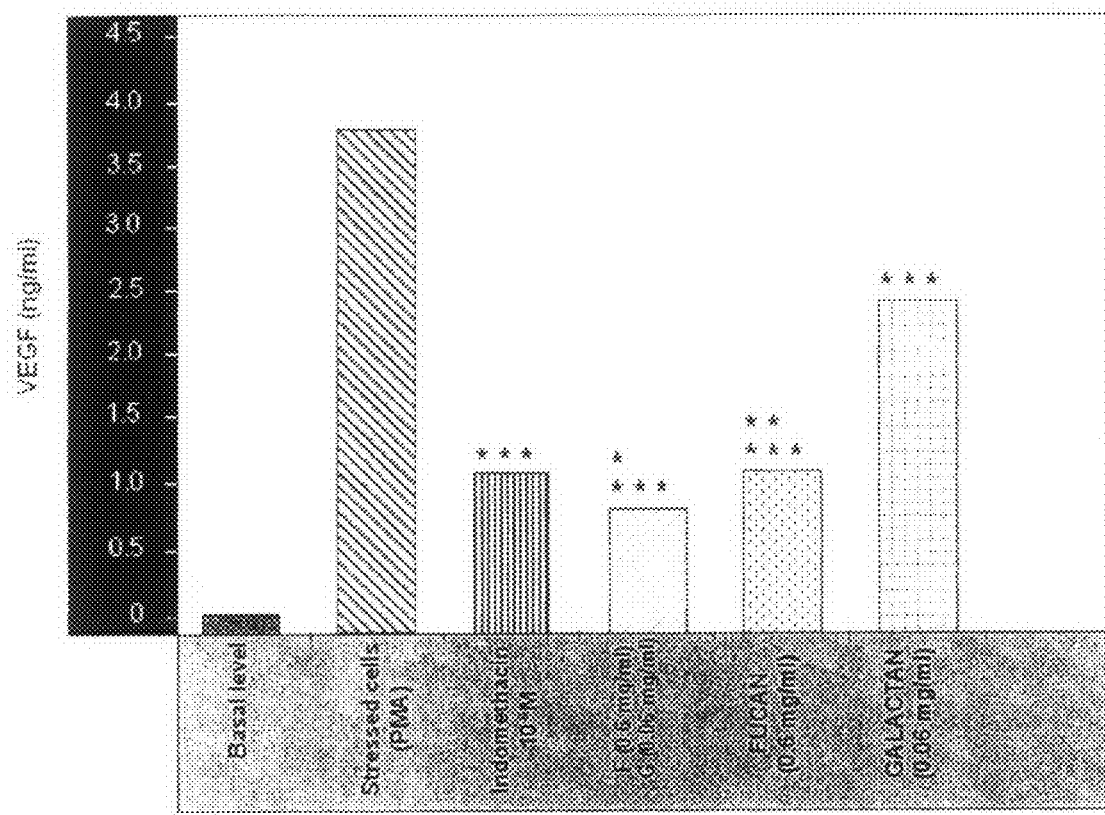
FIG. 1 depicts the effect of a fucans/galactans composition of the present invention on VEGF expression in human keratinocytes in vitro.

Fucans from various algae may be prepared by known methods and the resulting purified products, fucans-containing products can be used in the present invention.

In a specific embodiment, fucans of the present invention are obtained from *Ascophyllum nodosum*. In their native form, fucans are constituted by a heterogenous population of molecules principally composed of sulfated L-fucose polymers that have high molecular weights, and are associated with uronic acids. In addition, several studies clearly show that *Ascophyllum nodosum* fucans possess large portion of both α(1→3) and α(1→4) glycosidic bonds.

Native Fucans (i.e. which Naturally Contain Minerals)

Fresh, frozen or dried clean algae can be transformed into a fine powder. Fresh and frozen algae are preferably chopped to obtain a particle size smaller than about 8 mm, preferably between about 0.5 mm and about 8 mm, most preferably about between about 2 and about 5 mm.

The algae could be chopped with instruments including but not limited to, a meat chopper, kitchen homogenizer, Polytron™ disintegrator and any commercial cutter. Variation and adjustment of the crushing parameters are well within the knowledge of the skilled artisan, merely depending on the volume of homogenate and of the equipment used.

Fucans may be extracted from the chopped algae by an adequate volume of water-based solution. The volume of solution used can be increased without bearing any deleterious effect on the recovery yield of valuable components. A small volume is preferred since it is more convenient to manipulate than larger volumes. Water may be purified by inverse osmosis and multiple filtrations down to 0.1 micron filter. Many aqueous solutions (containing salts, for example) could be used in lieu of water. When recovery of a plurality of hydrosoluble activities is contemplated, working at a near neutral pH (5.0 to 8.0) and in non-denaturing conditions is preferred to avoid degradation or denaturation of some of the active components. For the sake of clarity, any extraction medium that is compatible with the preservation of biologically active fucans components is within the scope of this invention. Therefore, performing the extraction in pure water is preferred. Other preferred embodiments include those wherein salts and/or chaotropic agents are added to the water prior to or during extraction.

The extraction may be performed at about 60 to about 95 degrees Celsius, preferably between about 80 to 95 degrees Celsius. The extraction time is generally about 12 to 24 hours, preferably between about 10 and about 16 hours. The speed of the agitation as well as the volume of aqueous solution may influence both time and yield of extraction.

The supernatant is then separated from the pellet. The separation can be quickly performed by filtration (with a mesh of about 50 micrometer), centrifugation, or with a commercial decanter. Variation and adjustment of the separation parameters are well within the knowledge of the skilled artisan, merely depending on the volume of homogenate and of the equipment used.

The resulting supernatant is then clarified to get rid of fine suspension susceptible of affecting the performance of the process. The clarification is performed at a temperature ranging from about 50 to about 80 degrees Celsius, preferably at about 40 to about 60 degrees Celsius The clarified material is then cooled down at a temperature ranging from about 15 to about 30 degree Celsius, preferably from about 15 to about 25 degrees Celsius.

The clarified material is then acidified at about pH 2 to precipitate proteins and alginates. For example, the acidification could be performed in presence of sulfuric acid or hydrochloric acid. The acidified materiel is then clarified as described above. The solution is then neutralized.

The neutralized solution is then concentrated. This step can be performed by different means including but not limited to: dialysis, chromatography (adsorption, ionic exchange, gel filtration), electrophoresis, ultrafiltration, ultra centrifugation with zonal density gradients, adsorption and extraction.

In a specific embodiment, the solution may be ultrafiltered at about 4 degrees Celsius to 25 degrees Celsius (although temperature could be increased to about 40 degrees Celsius) on a tangential flow filtration column. Column membrane porosity is about 500 kDa, preferably 300 kDa, most preferably 100 kDa. The obtained fraction is then dialyzed which allows a first fractionated extract to be obtained, comprising hydrosoluble fucans of an average molecular weight generally lower than the membrane cut off taking into account the variability inherent to the membrane pores and to the conformation of the molecules in the extraction solvent. This inherent variability applies to any membrane used herein. This fraction will be further referred to as the native fucans fraction which is naturally mineralized (FHMW-M).

Molecular analysis of fucan fractions reveal that fucose constitutes between about 15 and 45% and more preferably between 20 and 35% of the dry weight. Moreover, 3 to 35% and more preferably 10 to 29% of the dry weight is composed of uronic acid. These fucans are richly sulfated, since 12 to 30% and more preferably 15 to 25% of the dry weight is composed of sulfates ($SO_4$) radical.

According to another embodiment, fucans could be extracted from the chopped algae by an adequate volume of water-based solution in presence of 1% calcium chloride. The extraction is performed at about 85 degree C. for about 4 hours. These conditions allow the proteins comprising alginates to precipitate. The resulting supernatant is collected, the polysaccharides are precipitated in the presence of ethanol and the fucans are further purified by ultrafiltration.

Depolymerized Fucans

The fucans could be used entirely or partly in their depolymerized form. In a specific embodiment, the fucans' depolymerization is performed by acidic hydrolysis. Native fucans (FHMW-M) are acidified to a pH of about 0.5 to about 2.0, preferably to about 0.5 to about 1.0. The acidified solution is incubated at temperature of about 55 to about 70 degree C. for about 4 hours. Depolymerization may be achieved by different methods including but not limited to: ultrasounds; UV radiations; ozonolysis; chemical, radical, or enzymatic hydrolysis; and high pressure and temperature.

The solution is then neutralized with NaOh and then concentrated/purified by ultrafiltration followed by a dialysis.

The fucans present in the solution are then precipitated in the presence of alcohol and the precipitate is dried. Variation and adjustment of the parameters for alcohol precipitation and drying are well within the knowledge of the skilled artisan, merely depending on the volume of the solution and on the equipment used. The fraction obtained contains hydrosoluble fucans of an average molecular weight ranging between about 5 kDa and about 25 kDa. This fraction will be further referred to as the mineralized depolymerized fucan fraction (FLMW-M).

Demineralised Fucans

The fucans fractions could further be used entirely or partly in their demineralised form. Demineralisation could be industrially performed, such as with but not limited to nanofiltration. The nanofiltration process is a reverse osmosis process using a relatively open RO membrane, allowing water and small univalent ions ($Na+$, $K+$, $Cl-$) to pass. Variation and adjustment of the parameters for nanofiltration are well within the knowledge of the skilled artisan, merely depending on the volume of the solution and of the equipment used. This fraction will be further referred to as FHMW or FLMW depending on whether the fucans fraction is native or depolymerized, respectively.

Preparation of Galactans

In a specific embodiment, galactans of the present invention are obtainable from *Asparagopsis armata*, cultured according to the patent application EP-0733636 A1. This patented cultivation technique is based on the principles of vegetative algal propagation, and the use of a special type of rope. This unique rope is seeded with segments of wild thalli which then proliferate by vegetative propagation/fragmentation and significantly increase in biomass.

Fresh, frozen or dried clean algae can be transformed into a fine powder. Fresh and frozen algae are chopped to obtain particle size smaller than about 8 mm, preferably between about 0.5 mm and about 8 mm, most preferably between about 2 and about 5 mm as described above.

Native Galactans (i.e. Which Naturally Contain Minerals)

Galactans are extracted from the chopped algae by an adequate volume of water-based solution. The volume of solution used can be increased without bearing any deleterious effect on the yield of recovery of valuable components. A small volume is preferred since it is more convenient to manipulate than larger volumes. Water is then purified by inverse osmosis and multiple filtrations down to 0.1 micrometer filter. Many aqueous solutions (containing salts, for example) could be used in lieu of water. When recovery of a plurality of hydrosoluble activities is contemplated, working at a near neutral pH (6.0 to 8.0) and non-denaturing conditions is preferred to avoid degradation or denaturation of some of the active components. For the sake of clarity, any extraction medium that is compatible with the preservation of biologically active galactan components is within the scope of this invention. Therefore, performing the extraction in pure water is preferred. Other preferred embodiments include those wherein salts and/or chaotropic agents are added to the water prior to or during extraction.

The extraction is performed at about 50 to about 90 degrees Celsius, preferably ranging between about 60 to about 80 degrees Celsius. The extraction time is about 1 to 8 hours, preferably between about 4 and 6 hours. The speed of the agitation as well as the volume of aqueous solution may influence both time and yield of extraction.

The supernatant is then separated from the pellet. The separation can be quickly performed by filtration (with mesh of about 50 micrometer), centrifugation, or with a commercial decanter. Variation and adjustment of the separation parameters are well within the knowledge of the skilled artisan, merely depending on the volume of homogenate and of the equipment used.

The resulting supernatant is then clarified to get rid of fine suspension susceptible to affect the performance of the process. The clarification was performed at a temperature ranging from about 50 to about 70 degrees Celsius, preferably at about 60 degrees Celsius.

The clarified material is then cooled down at a temperature ranging from about 30 to about 50 degrees Celsius, preferably from about 40 degrees Celsius.

The clarified material is then acidified at a pH ranging from about 3 to about 5, preferably about 4.5. For example, the acidification could be performed in presence of sulfuric acid or hydrochloric acid. The acidified materiel is then clarified as described above.

The acidified materiel is then depigmented by microfiltration and then clarified as described above. Variation and adjustment of the parameters for microfiltration are well within the knowledge of the skilled artisan, merely depending on the volume of the solution and of the equipment used. The solution is then neutralized.

The depigmented solution is then concentrated. This step can be performed by different means including but not limited to: dialysis, chromatography (adsorption, ionic exchange, gel filtration), electrophoresis, ultrafiltration, ultra centrifugation with zonal density gradients, adsorption and extraction.

In a specific embodiment, the solution is ultrafiltered at about 4 degrees Celsius to about 25 degrees Celsius (although temperature could be increased to about 40 degrees Celsius) on a tangential flow filtration column having a membrane of a porosity of about 10 kDa. The obtained fraction is then dialyzed which allows a first fractionated extract to be obtained, comprising hydrosoluble galactans of an average molecular weight generally higher than the membrane cut off taking into account the variability inherent to the membrane pores and to the conformation of the molecules in the extraction solvent higher than the membrane cut off.

The galactans present in the solution are then precipitated in the presence of alcohol and the precipitate is dried. Variation and adjustment of the parameters for alcohol precipitation and drying are well within the knowledge of the skilled artisan, merely depending on the volume of the solution and of the equipment used. This galactan-enriched fraction will be further referred to as the mineralized galactan fraction (GHMW-M).

Molecular analysis of galactans fractions obtained from red algae revealed that galactose constitutes between about 15 and 95%, preferably between about 20 and 75%, and more preferably between about 30 and 40% of the dry weight of the galactans. Moreover, 1 to 10%, and more preferably 1-5% of the dry weight is composed of uronic acid. These galactans are richly sulfated, since about 1 to 60% and more preferably about 20 to 35% of the dry weight is composed of sulfates ($SO_4$) radical.

Enzymatic Dosage of D-Galactose

The dosage of D-galactose is performed with a dosage kit (test combining lactose/D-galactose, Boehringer Mannheim n. E0176303). D-galactose is oxydized at pH 8.6 by beta-galactose dehydrogenase (Gal-DH), in the presence of NAD (nicotinamide adenine Dinucleotide).

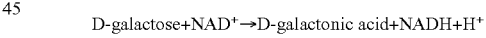

$$D\text{-galactose} + NAD^+ \rightarrow D\text{-galactonic acid} + NADH + H^+$$

The reaction being stoichiometric, the quantity of NADH formed is equivalent to the quantity of oxydized D-galactose. It is followed by a measure of absorbance at 340 nm. A standard curve is realized from D-galactose. 15 mg of polysaccharides are hydrolized by 1 mL of trifluoroacetic acid 2 M during 90 minutes at 120° C. 20 mg of D-galactose are also hydrolized in the same conditions. Hydrolysates are evaporated three times at Rotavapor™, using each time in distilled water and redissolved in 10 ml of milliQ™ for the polysaccharide or in 100 ml of milli-Q water for the D-galactose. The pH of these two solutions is then adjusted at 6.6 (i.e. pH of the citrate buffer of the dosage kit) with the assistance of sodium hydroxide 0.05 M. 100 and 200 µL of the polysaccharides solution at a concentration of 1.5 mg·mL$^{-1}$ are placed in glass tubes and assayed according to the manufacturer's instructions. 100 to 500 µL of the solution of D-galactose at a final concentration of 0.2 g·L$^{-1}$ are used to produce the standard curve. The absorbance is read after 45 minutes at a wavelength of 340 mm, and the D-galactose amount found in the polysaccharide is measured in light of the standard curve. Knowing the total quantity of galactose contained in the polysaccharide (dosed in the form of alditols acetates.) the L-galactose amount in the polysaccharides may be derived.

Determination of Sulphate Content and Uronic Acid Content of Extracted Fucans and Galactans Total sugars and uronic acids were quantified on each polysaccharide using phenol-sulfuric acid method (Dubois et al., 1956) using glucose as standard and Blumenkrantz method (Blumenkrantz and Asboe-Hansen, 1973) with glucuronic acid as standard and 3-phenyl-phenol as reagent. Absorbance measurements were realised in triplicate. Microplate reader (Molecular devices, Ottawa, ON, Canada) was used for total sugars analysis and HP-8453 spectrophotometer (Hewlett Packard, Mississauga, ON, Canada) equipped with UV-visible ChemStation™ software for uronic acids. Minerals ($Ca^{2+}$, $MG^{2+}$, $Na^+$ and S) were quantified by ICP-OES (Inductively Coupled Plasma-Optical Emission Spectroscopy) with model Optima™ 4300 DV from Perkin-Elmer (USA) equipped with Winlab32™ software. Sulphates content was deduced from the amount of sulphur determined by ICP described by this relation: % sulphate group=3.22×S (Roger et al., 2004).

Estimation of the Molecular Weight of Polysaccharides Formed by HPSEC (High Performance Size Exclusion Chromatography)

The molecular mass of oligosaccharides formed by radicalar depolymerization is determined by high performance steric exclusion. It allows to evaluate the number average molecular weight (Mn) each oligosaccharides, molecular weight at the peak (Mp), and the polydispersity indicia (Ip) (=Mw/Mn) which characterize the polysaccharides chains homogeneity. The calibration is obtained with pullulan standards (Nardella et al., 1996). Pullulans are glucanes, namely neutral polysaccharides, while oligosaccharides from *Asparagopsis armata* are highly sulfated. This is the reason why the estimated mass of *Asparagopsis armata* oligosaccharides can be assimilated to equivalent pullulans masses but does not reflect the real mass of these oligosaccharides. This method is also very useful to compare various fractions obtained during radicalar depolymerization performed in different conditions. The protocol used is described in Mulloy et al. (1997). The TSK™ G3000 SW-XL and TSK™ G2000 SW-XL columns in series were used. The eluting agent is a solution of ammonium acetate at 0.1 M, and the flow rate applied is of $0.5\ mL \cdot min^{-1}$. The detection is made by refractometry (refractomonitor W, LDC, Analytical, Stone, Saffs., UK). The data treatment is made by a software from Polymer Laboratories, Church Stretton, UK.

In accordance with a specific embodiment of the present invention, the galactans fraction was characterized by the method described above. According to such method, galactose constituted about 37% of the dry weight of the fraction, uronic acid constituted about 3% of the dry weight of the fraction, and sulfates constituted about 27% of the dry weight of the fraction. The average molecular weight of these galactans was higher than about 100 kDa and in more specific embodiments, the Mw was about 350 kDa (obtained from a pullulan equivalent).

Depolymerized Galactans

The galactans could be used entirely or partly in their depolymerized form. In a specific embodiment, the galactans' depolymerization is performed by acidic hydrolysis. Native galactans are acidified to a pH of about 0.5 to about 2.0, preferably to about 0.5 to about 1.0. The acidified solution is incubated at temperature of about 55 to about 70 degree C. for about 4 hours. Depolymerization may be achieved by different methods including but not limited to: ultrasounds, UV radiations, ozonolysis, chemical, radical, or enzymatic hydrolysis, and high pressure and temperature.

The solution is then neutralized and then concentrated/purified on a 2 kDa ultrafiltration followed by a dialysis.

The galactans present in the solution are then precipitated in the presence of alcohol and the precipitate is dried. Variation and adjustment of the parameters for alcohol precipitation and drying are well within the knowledge of the skilled artisan, merely depending on the volume of the solution and of the equipment used. This fraction will be further referred to as the mineralized depolymerized galactans fraction (GLMW-M).

Demineralized Galactans

The galactans fractions could also be used entirely or partly in their demineralised form. Demineralization could be industrially performed such as with but not limited to nanofiltration as described above. This fraction will be further referred to as GHMW.

The present invention is illustrated in further details by the following non-limiting examples.

EXAMPLE 1

Preparation of Fucans

Fucans were obtained from *Ascophyllum nodosum*. Fresh and frozen algae were chopped to obtain a particle size between 2 and 5 mm.

Fucans were extracted from the chopped algae in a water-based solution.

The extraction of fucans was performed at a temperature varying from 80 to 95 degrees Celsius for a time of 10 to 16 hours.

The supernatant was then separated from the pellet with a commercial decanter.

The resulting supernatant was then clarified to get rid of fine suspension susceptible to affect the performance of the process. The clarification was performed at 60 degrees Celsius The clarified material was then cooled down at 25 degrees Celsius and was then acidified at pH 2 to precipitate proteins and alginates. The acidified materiel was then clarified and neutralized as described above.

The neutralized solution was then purified/concentrated by ultrafiltration and dialysis to obtain a fraction containing fucans with average molecular weight higher than 100 kDa to obtain a naturally mineralized native fucans fraction (FHMW-M).

Depolymerized Fucans

The fucans depolymerization was performed by acidic hydrolysis. Native fucans (FHMW-M) were acidified to a pH ranging from 0.5 to 1.0. The acidified solution was incubated at 65 degrees Celsius for 4 hours. The solution was then neutralized and concentrated as described above.

The fucans present in the solution were then precipitated in the presence of ethanol and the precipitate was dried to obtain a mineralized depolymerized fucan fraction (FLMW-M). Fucans average molecular weight was generally ranging from about 5 kDa to about 25 kDa.

Demineralized Fucans

Demineralization was performed by nanofiltration to obtain the FHMW or FLMW fraction depending on whether the fucans fraction was native or depolymerized.

Molecular Analysis of Fucans

The molecular analysis of the FHMW-M fraction revealed that fucose constituted between 25 and 35% of the dry weight. Moreover, 12 to 20% of the dry weight was composed of uronic acid. These fucans are richly sulfated, since 15 to 25% of the dry weight was composed of sulfates ($SO_4$) radical.

EXAMPLE 2

Preparation of Galactans

Galactans were obtained from Asparagopsis armata, which were cultured according to the patent application EP-0733636 A1 as described above.

Fresh and frozen algae were chopped to obtain particle size smaller between 0.5 and 2 mm.

Galactans were extracted in water at pH 8 and at a temperature ranging from 60 to 80 degrees Celsius for about 4 to 6 hours.

The supernatant was then separated from the pellet with a commercial decanter. The resulting supernatant was then clarified to get rid of fine suspension susceptible to affect the performance of the process. The clarification was performed at 60 degrees Celsius The clarified material was then cooled down at 40 degrees Celsius and the pH was adjusted at 4.5.

The acidified material was then depigmented by tangential microfiltration (1.2 micrometer).

The depigmented solution was then concentrated/purified through ultrafiltration with a tangential flow filtration column having a membrane of a porosity of 10 kDa. The obtained fraction was then dialyzed so as to obtain a fraction containing molecules of higher than about 100 kDa. The galactans present in the solution were then precipitated in presence of alcohol and the precipitate was dried to obtain a native galactans fraction that is naturally mineralized (GHMW-M).
Demineralized Galactans The galactans fractions could be used and prepared entirely or partly in their demineralised form. Demineralisation was performed by nanofiltration as described above to obtain a mineralized demineralized galactans fraction (GHMW).
Molecular Analysis of Galactans The molecular analysis of the GHMW fraction obtained from these red algae revealed that galactose constituted about 37% of the dry weight. Morever, 3% of the dry weight was composed of uronic acid. These galactans were richly sulfated, since about 27% of the dry weight was composed of sulfates ($SO_4$) radical.

EXAMPLE 3

Description of Fucans and Galactans Fractions

The different fractions prepared and tested either separately or in combinations are summarized in Table 3 below.

TABLE 3

DESCRIPTION OF THE DIFFERENT FUCAN AND GALACTAN FRACTIONS

| | |
|---|---|
| FHMW | This preparation contains native sulfated-fucans, having an average molecular weight ranging from about 0.1 kDa to about 100 kDa. This fraction was demineralized by nanofiltration. |
| FLMW | Preparation containing depolymerized sulfated-fucans, which was demineralized by nanofiltration. The average molecular weight of these fucans is ranging from about 5 kDa to about 25 kDa. This preparation was demineralized by nanofiltration. |
| FLMW-M | Preparation containing depolymerized sulfated-fucans which was not demineralized. The average molecular weight of these fucans is ranging from about 5 kDa to about 25 kDa. |

TABLE 3-continued

DESCRIPTION OF THE DIFFERENT FUCAN AND GALACTAN FRACTIONS

| | |
|---|---|
| FHMW-M | Preparation containing native sulfated-fucans (i.e. before concentration and nanofiltration). The average molecular weight of the fucans present in this fraction is from about 0.1 kDa to about 100 kDa. |
| GHMW | Preparation containing native galactans. The average molecular weight of these galactans is higher than about 100 kDa. This preparation was demineralized by nanofiltration. |
| GHMW-M | Preparation containing native galactans, which was not demineralized. The average molecular weight is higher than about 100 kDa. |

EXAMPLE 4

Hen's Egg Chorioallantoic Membrane Test for Irritation Potential of Fucans/Galactans Mixtures The Hen's Egg Test (HET) is a rapid and sensitive toxicity test and can give information on mucous-membrane irritation potencies of chemical substances. Testing with incubated hen's eggs is a borderline case between in vivo and in vitro systems. A specific score and classification scheme was developed for the HET.

The ocular irritancy potential of a composition containing 50 mg/ml of FLMW and 5 mg/ml of GHMW was tested at 0.2% (0.11 mg/ml) was performed as previously described by Luepke and Kemper (Luepke N P & Kemper F H (1985) Hen's egg chorloallantoic membrane test for irritation potential Food Chem. Toxicol. 1985 (2):287-291). Briefly, the tested compositions were applied to the chorio allantoic membranes for 20 seconds then rinsed off with NaCl 0.9% (w/v). Injection, hemorrhage and coagulation parameters were scored during 5 minutes after treatment. The control preparations containing lauryl sulfo betain at 3.2%, 0.4% were classified as irritant while the 0.05% preparation was classified as practically non irritant, for the chorioallantoic membrane of chicken egg. The tested composition was classified as non irritant for the chorioallantoic membrane of chicken egg.

EXAMPLE 5

Effect of Polysaccharides Compositions on IL-8, PGE2 and VEGF Levels in Human Keratinocytes In Vitro Recent publications have shown that PMA activation led normal keratinocytes to produce increased amounts of interleukin-8 (IL-8), a mediator of inflammation (Chabot-Fletcher et al. (1994) J. Invest. Dermatol. 103:509-515). Moreover, psoriatic keratinocytes produce very high amounts of IL-8, which further promote neovascularization in psoriatic plaques (Nickoloff et al. (1994) Am. J. Pathol. 144:820-828).

As indicated above, VEGF is a multifunctional agent. It is a potent vascular permeabilization agent that renders the endothelial tissue hyperpermeable, leading to the extravasation of plasma proteins and leukocytes migration to the inflammatory site. It is also a multifunctional angiogenic growth factor that stimulates the endothelial cells to proliferate and to migrate.

Inhibition of the production of IL-8 and VEGF in PMA-activated keratinocytes was taken to indicate herein that tested polysaccharide compositions have anti-inflammatory and anti-extravasation activities.

Human keratinocytes (NCTC2544) were cultured in DMEM containing 5.5 mM glucose, 2 mM L-glutamine, and 10% FCS. Cells were pre-treated with various fucan/galactan polysaccharides compositions of the invention (0.06-2.4 mg/ml, unless otherwise indicated) during 24 hours. Afterward, the culture media were replaced for one containing the polysaccharides compositions in the presence of 0.1 µg/ml of Phorbol 12-Myristate 13-acetate (PMA). Twenty four hours later the culture media were collected for further analysis. VEGF, IL-8, $PGE_2$ contents in the culture media were assayed by ELISA using commercial kit from Diaclone inc. and R&D systems inc.

TABLE 4

EFFECT OF VARIOUS POLYSACCHARIDE COMPOSITIONS ON IL-8, $PGE_2$ AND VEGF LEVELS IN HUMAN KERATINOCYTES IN VITRO

| | | Effect on PMA-treated cells | | |
|---|---|---|---|---|
| Treatment | Concentration | IL-8 (% inhibition) | $PGE_2$ (% inhibition) | VEGF (% inhibition) |
| FHMW | 2.4 mg/ml | 6 | 62** | 74** |
| | 1.2 mg/ml | 7 | 63** | 71** |
| | 0.6 mg/ml | 4 | 59** | 71** |
| FLMW | 2.4 mg/ml | 0 | 64** | 73** |
| | 1.2 mg/ml | 18** | 66** | 75** |
| | 0.6 mg/ml | 22** | 64** | 74** |
| GHMW | 0.24 mg/ml | 9 | 49** | 40** |
| | 0.12 mg/ml | 9 | 45** | 32** |
| | 0.06 mg/ml | 5 | 34** | 35** |
| FHMW/ GHMW (40/1 w/w) | 1.96 mg/ml | 0 | 62** | 71** |
| | 0.984 mg/ml | 15* | 60** | 70** |
| | 0.492 mg/ml | 15 | 66** | 69** |
| FHMW/ GHMW (10/1 w/w) | 1.32 mg/ml | 8 | 57** | 72** |
| | 0.66 mg/ml | 11 | 62** | 70** |
| | 0.33 mg/ml | 30** | 65** | 71** |
| FHMW/ GHMW (2.5/1 w/w) | 0.672 mg/ml | 15** | 59** | 73** |
| | 0.336 mg/ml | 16** | 64** | 71** |
| | 0.168 mg/ml | 24** | 64** | 71** |
| FLMW/ GHMW (40/1 w/w) | 1.96 mg/ml | 28** | 67** | 74** |
| | 0.984 mg/ml | 34** | 70** | 69** |
| | 0.492 mg/ml | 42** | 69** | 73** |
| FLMW/ GHMW (10/1 w/w) | 1.32 mg/ml | 15 | 69** | 81** |
| | 0.66 mg/ml | 13 | 70** | 79** |
| | 0.33 mg/ml | 26** | 75** | 80** |
| FLMW/ GHMW (2.5/1 w/w) | 0.672 mg/ml | 6 | 68** | 79** |
| | 0.336 mg/ml | 22** | 72** | 76** |
| | 0.168 mg/ml | 26** | 71** | 76** |
| FHMW-M | 4 mg/ml | 0 | 97** | 39** |
| | 2 mg/ml | 49** | 98** | 21** |
| | 1 mg/ml | 40** | 98** | 14 |
| FLMW-M | 4 mg/ml | 30** | 64 | 73** |
| | 2 mg/ml | 38** | 70 | 73** |
| | 1 mg/ml | 45** | 68 | 72** |

*P < 0.05
**P < 0.01

The results indicated that PMA strongly upregulates the production of VEGF in keratinocytes. Indomethacin, a non-selective cyclooxygenase inhibitor, partially inhibits PMA-induced VEGF expression. This suggests that the PMA-induced VEGF production is not solely dependent on the cyclooxygenase pathway and that other mediators might be involved. This is in line with what has been observed by Trompezinski and collaborators (Trompezinski S, Pernet I, Schmitt D, Viae J. Inflamm Res. 2001; (50):422-427).

The results also showed that fucans/galactans compositions of the present invention are able to significantly inhibit PMA-induced keratinocyte activation of VEGF and IL-8. For example, a concentration of 0.66 mg/ml of the fucans/galactans (10/1) reduces by 79% (p<0.01) the VEGF production (see FIG. 1). Without being so limited, these results do not exclude the hypothesis that the action of this composition aims at more than one stress-induced signalling pathway in skin cells. Fucans and galactans compositions were also tested individually at a concentration equivalent to that found in the fucans/galactans combination tested. Fucans are more effective than galactans in reducing the PMA-induced production of VEGF. However, there is an unexpected synergistic effect of the fucans/galactans composition in inhibiting VEGF (see FIG. 1). Indeed, there is a significant difference (p<0.05) between the effect of the fucans/galactans composition and the effect of the individual sulfated-fucans or galactans in inhibiting the PMA-induced increase in VEGF. Similar results were observed with IL-8 (see Table 4).

Results also showed that $PGE_2$ production is highly increased in keratinocytes upon a stress induced by the pro-inflammatory agent PMA. Indomethacin, a non-selective cyclooxygenase inhibitor, displays a complete inhibition of the PMA-induced $PGE_2$ expression.

Figure 2:
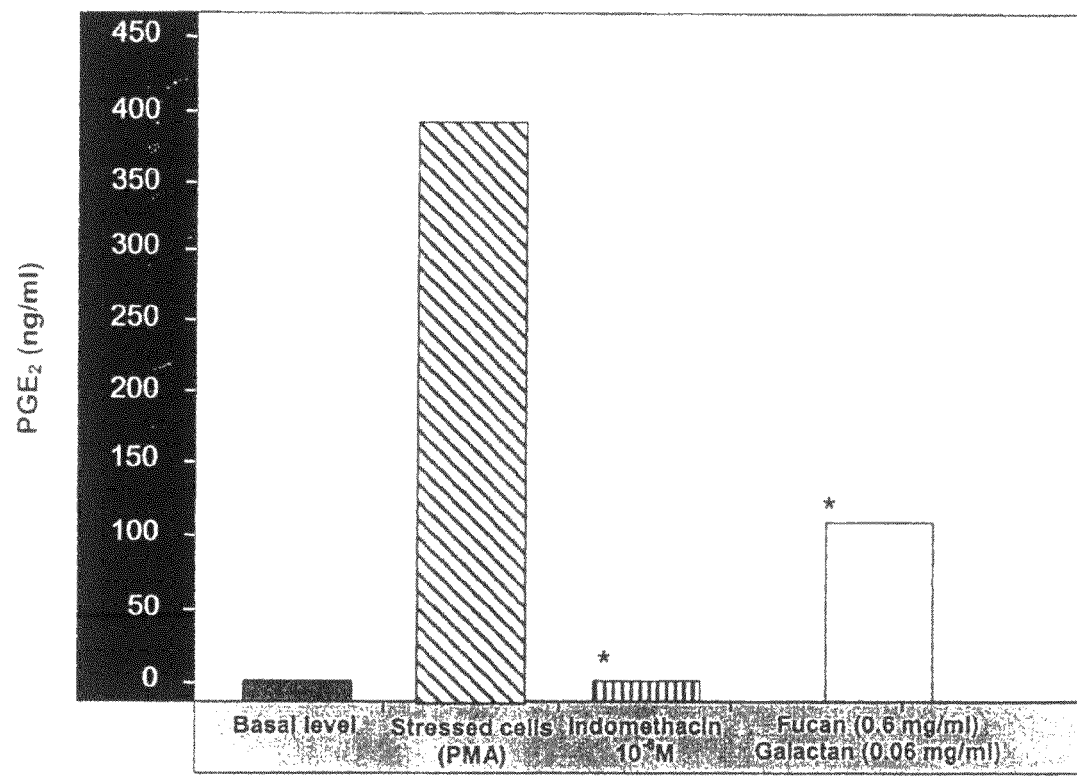
FIG. 2 depicts the effect of a fucans/galactans composition of the present invention on $PGE_2$ expression in human keratinocytes in vitro.

Fucans/galactans compositions of the present invention are able to significantly inhibit $PGE_2$ release from PMA-treated keratinocytes. For example, a concentration of 0.66 mg/ml of the fucans/galactans (10/1) composition significantly reduces (70% reduction, see FIG. 2) $PGE_2$ production. The effect of the demineralised compositions was not higher than the sulfated-fucans and galactans alone. The inhibition by FHMW-M was however close to 100%. Mineralized molecules may thus substitute for at least a part of the demineralized polysaccharides and provide better compositions.

Results obtained with human keratinocytes demonstrate that the fucans/galactans composition inhibits the induction of VEGF and $PGE_2$ in human keratinocytes. $PGE_2$ is a prostaglandin that mediates microcapillary dilatation (Rhodes L E, Belgi G, Parslew R, McLoughlin L, Clough G F, Friedmann P S. J Invest Dermatol. 2001 October; 117(4):880-5: Rhodes L E, Belgi G. Parslew R, McLoughlin L, Clough G F, Friedmann P S. J Invest Dermatol. 2001 October; 117(4):880-5) and VEGF is a growth factor that plays a primary role in the phenomenon of microcapillary hyperpermeability (Brauchle M, Funk J O, Kind P, Werner S. J Biol chem. 1996 Sep. 6; 271(36):21793-7; Dvorak H F, Brown L F, Dvorak A M. Am J. Pathol. 1995 May; 146(5):1029-39). Even though the VEGF and $PGE_2$ pathways may be interrelated especially when up-regulated by various stresses (Harada S, Nagy J A, Sullivan K A, Thomas K A, Endo N, Rodan G A, Rodan S B. J clin Invest. 1994 June; 93(6):2490-6; Cheng T, Cao W, Wen R, Steinberg R H, LaVail M M. Invest Opthalmol V is Sci. 1998 March; 39(3):581-91; Trompezinski S, Pernet I, Schmitt D, Viae J. Inflamm Res. 2001; (50):422-427), there are indications that, at least in part, they obey to independent and different upstream signal transduction pathways (Trompezinski S, Pernet I, Schmitt D, Viae J. Inflamm Res. 2001; (50):422-427, Bachelor M A, Bowden G T. Seminars in Cancer Biology. 2004; 14:131-138). Those observations demonstrate the need to simultaneously inhibit VEGF and $PGE_2$ pathways to prevent stress-induced skin photo-damage.

EXAMPLE 6

Effect of Polysaccharides Compositions on Human Keratinocytes

Viability In Vitro

Human keratinocytes (NCTC2544) were cultured in DMEM containing 5.5 mM glucose, 2 mM L-glutamine, and 10% FCS. Cells were pre-treated with polysaccharides compositions (0.06-2.4 mg/ml, Unless otherwise indicated) during 24 hours. Afterward, the culture media were replaced for one containing the polysaccharides compositions in the presence of 0.1 μg/ml of Phorbol 12-Myristate 13-acetate (PMA). Cell's viability was determined by measuring the activity of mitochondrial dehydrogenase (MTT Cell Proliferation Assay). The MTT Cell Proliferation Assay measures the cell proliferation rate and conversely, when metabolic events lead to apoptosis or necrosis, the reduction in cell viability. The assay is based upon the capacity of the mitochondrial dehydrogenase to reduce the yellow tetrazolium MTT (3-(4,5-dimethylthiazolyl-2)-2,5-diphenyltetrazolium bromide), to generate reducing equivalents such as NADH and NADPH. The resulting intracellular purple formazan can be solubilized and quantified by spectrophotometric means.

TABLE 5

EFFECT OF FUCANS AND GALACTANS PREPARATIONS
ON HUMAN KERATINOCYTES VIABILITY IN VITRO

| Polysaccharide preparation | Concentration | Cell's viability % of MTT conversion |
|---|---|---|
| FHMW | 2.4 mg/ml | 96 |
|  | 1.2 mg/ml | 98 |
|  | 0.6 mg/ml | 98 |
| FLMW | 2.4 mg/ml | 101 |
|  | 1.2 mg/ml | 98 |
|  | 0.6 mg/ml | 92 |
| GHMW | 0.24 mg/ml | 78 |
|  | 0.12 mg/ml | 77 |
|  | 0.06 mg/ml | 71 |
| FHMW/GHMW (40/1 w/w) | 1.96 mg/ml | 101 |
|  | 0.984 mg/ml | 99 |
|  | 0.492 mg/ml | 100 |
| FHMW/GHMW (10/1 w/w) | 1.32 mg/ml | 107 |
|  | 0.66 mg/ml | 106 |
|  | 0.33 mg/ml | 100 |
| FHMW/GHMW (2.5/1 w/w) | 0.672 mg/ml | 104 |
|  | 0.336 mg/ml | 109 |
|  | 0.168 mg/ml | 105 |
| FLMW/GHMW (40/1 w/w) | 1.96 mg/ml | 105 |
|  | 0.984 mg/ml | 98 |
|  | 0.492 mg/ml | 99 |
| FLMW/GHMW (10/1 w/w) | 1.32 mg/ml | 103 |
|  | 0.66 mg/ml | 111 |
|  | 0.33 mg/ml | 103 |
| FLMW/GHMW (2.5/1 w/w) | 0.672 mg/ml | 105 |
|  | 0.336 mg/ml | 106 |
|  | 0.168 mg/ml | 102 |
| FHMW-M | 4% | 82 |
|  | 2% | 86 |
|  | 1% | 90 |
| FLMW-M | 4% | 85 |
|  | 2% | 97 |
|  | 1% | 100 |

*P < 0.05
**P < 0.01

Results showed that high molecular weight galactans slightly reduced the keratinocytes viability, while no difference in viability was observed in the fucans treated-cells. For example, 0.6 mg/ml of high molecular weigh galactans reduces the cell viability by 30% while no viability alteration was observed at concentrations of fucans as high as 2.4 mg/ml. Surprisingly, the effect of galactans on keratinocyte viability was entirely prevented by the presence of fucans.

EXAMPLE 7

Clinical Efficacy of the Fucans/Galactans Compositions in Maintaining the Microcapillary Integrity upon Skin UV Exposure In Vivo Increased dilation and the subsequent increase in microcapillary circulation is part of the thermoregulative system (Charkoudian, 2003; Marszalek, 1996; Kellogg, 1993). In the skin, this physiological reaction is under the control of so-called neurogenic transmitters (Kellogg, 2005, 2003 and 1998, Bennett, 2003). However, skin microcapillary dilation also occurs in response to various stresses. For instance, an increase in skin microcirculation in response to UV has also been demonstrated (Benrath, 2001; Terui, 2001; Nose, 1993; Frodin et al., 1988). This phenomenon of dilation not only correlates with an increase in microcapillary circulation but also with a plasma protein leakage and leukocytes efflux (Holzer, 1998).

The measurement of skin microcapillary circulation has been widely used to assess the cutaneous response to physiological and pathophysiological conditions such as in reaction to allergens, vasodilators and in cases of atypical dermatitis, rosacea and psoriasis (Hee Chul Eun, 1995). Measurement of skin microcirculation can be more sensitive than the visualization of erythema (Wahlberg, 1992) and can thus be utilized to assess changes in the skin microcapillary integrity.

A device was used to measure cutaneous microcirculation. The skin thermal conductivity (K) is directly proportional to the superficial cutaneous microcirculation and is based on the capacity with which: the heat is transported by skin microcirculation. In the case of biological measurements, there is a linear relationship between cutaneous microcirculation and thermal conductivity. This conductivity is measured with a specific thermal device (exemplified by Hematron™) which is applied directly onto the skin. Microcapillary dilation and the resulting increase of blood circulation will increase the skin thermal conductivity.

Clinical study—preventive action against UV-exposure: Subjects applied either the placebo or a formulation containing 5% of 5.5 mg/ml of FLMW/GHMW (10/1) composition, twice daily for a period of 7 days on separate skin areas (day −7 to Day 0). One skin area was left as is, with no application of products as a control. On Day 0, the Hematron™ was used to measure the baseline skin microcapillary circulation. On the same day, subjects were exposed to 1 MED of UV (Day 0, T0h). Five hours after UV exposure (Day 0, T5h), skin microcirculation was again measured on all skin areas.

Figure 3:
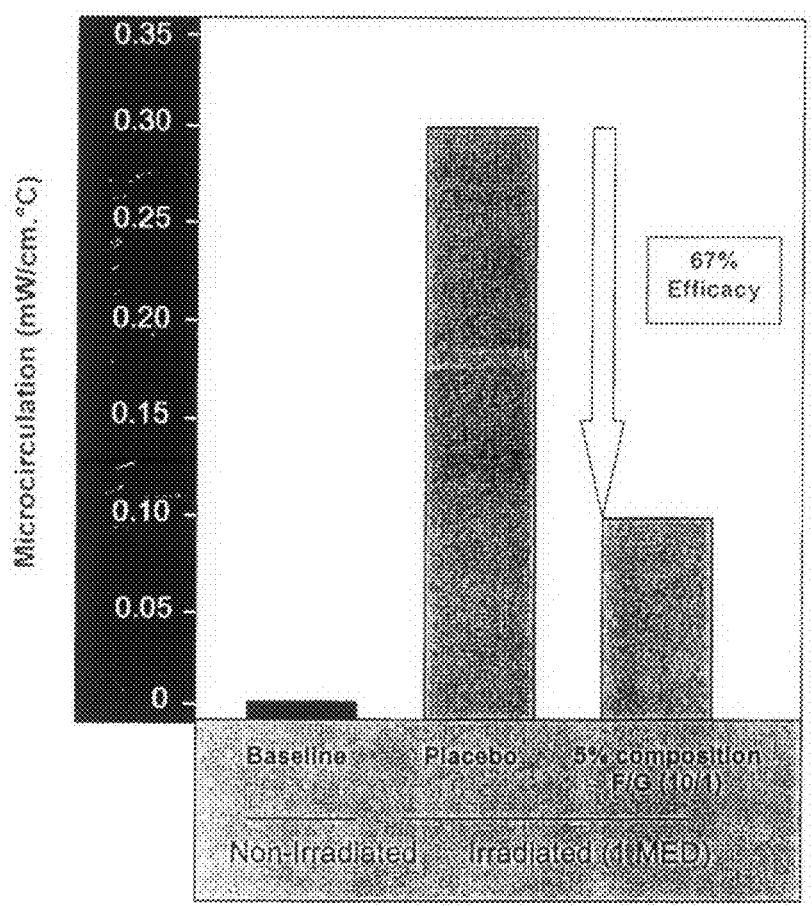
FIG. 3 depicts the preventive effect of a fucans/galactans composition of the present invention against skin UV exposure.

As illustrated in FIG. 3, results show that a topical formulation containing 5% of 5.5 mg/ml of FLMW/GHMW (10/1) in a topically acceptable carrier, namely a cream, was able to reduce the UV-induced increase skin microcirculation to a value close to what was observed in a non-irradiated skin area (baseline). The present formulation demonstrated an efficacy of 67% when applied as a preventive care.

Clinical Study—post UV exposure action: Subjects were first exposed to 1 MED of UV readily on Day 0. Five hours after UV exposure (Day 0, T5h), the Hermatron™ was used to assess the UV-induced increase in skin microcirculation. Subjects then applied either the placebo or a formulation containing 5% of 5.5 mg/ml of FLMW/GHMW (80/20) composition on irradiated areas (Day 0, T5h post UV). One skin area was left as is, with no application of products as a control. Two hours later, (Day 0, T7h) skin microcirculation was again measured on all skin areas.

Figure 4:
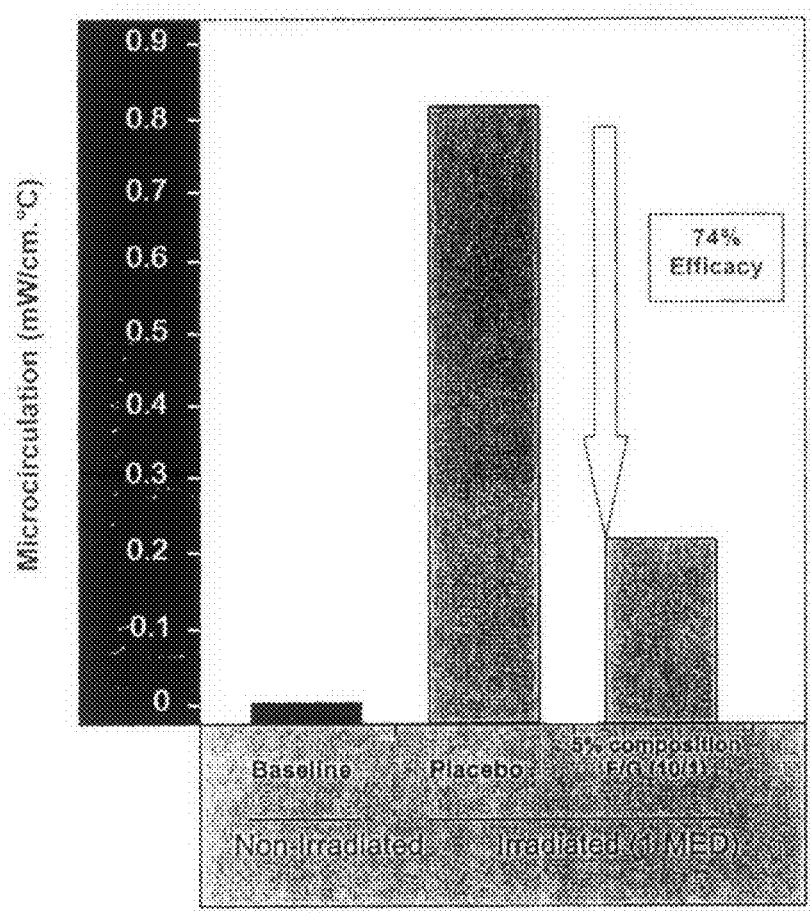
FIG. 4 depicts the effect of a fucans/galactans composition of the present invention after skin UV exposure.

As illustrated in FIG. 4, results show that a formulation containing 5% of 5.5 mg/ml of FLMW/GHMW (10/1) composition was able to reduce the UV-induced increase in skin microcirculation to a value close to what was observed for a non-irradiated skin area (baseline). The present formulation demonstrated an efficacy of 74% when applied post UV exposure.

EXAMPLE 8

Fucans/Galactans Formulations

Formulation 1

Demineralized water, Sepigel 305, Lanol 1688, Abil 8839, Irgasan DP300, Ethanol, Hydroxan ® CH, Phenonip Fucan/Galactan composition 0.1-99.9% of 5.5 mg/ml, JFL 544/2.

Formulation 2

Arlacel 165 ™, Arlacel 60 ™, Tween 60 ™, Sipol C16P ™, Crodamol OP, Miglyol 840 ™, Demineralized water, Sequestrene NA4 ™, Phenonip, Sepigel 305 ™, Fucan/Galactan composition 0.1-99.9% of 5.5 mg/ml.

Formulation 3

Arlacel P135 ™, Amerchol L10 ™, Amerlate P ™, Isohexadecane, Magnesium Stearate, Parsol MCX ™, Parsol 1789 ™, LNST ™ 98, Nipastat ™, Demineralized water, Eospoly UV cristal HL ™, Sequestrene NA4 ™, Cire DC 2501, Demineralized water, Magnesium Sulphate, Abil 8839 ™, Micropearl M100 ™, Fucan/Galactan composition 0.1-99.9% of 5.5 mg/ml, Lanachrys ™, Joyty Concentrate.

Formulation 4

Demineralized water, Carbopol Ultrez 10 ™, Amigel ™ (sol. 1% Aq. Phenonip, Demineralized water, TEA, Hydralphatine ™ 3P, Phenonip ™, Pure Ethanol, Abil 8839 ™, Joyty Concentrate, LRI Solubilizer, Fucan/Galactan composition 0.1-99.9% of 5.5 mg/ml.

Formulation 5

Cetyl alcohol (and) Glyceryl stearate (and) PEG-75 ™ stearate (and) Ceteth-20 ™ (and) Steareth-20 ™, Mineral oil (and) Lanolin alcohol, Isopropyl lanolate, Mineral oil (and) Prunus Armeniaca (Apricot) Kernel oil (and) Calendula officinalis flower extract, LNST ™ 98, Demineralized water, Carbomer ™ (2% aqueous solution), Red 33 (10% aqueous solution), Blue 1 (10% aqueous solution), Cyclopentasiloxane (and) cyclohexasiloxane, Demineralized water, Triethanolamine, Phenoxyethanol (and) Propylparaben (and) Butylparaben, Glycerin, Aluminium starch octenyl succinate, Fucan/Galactan composition 0.1-99.9% of 5.5 mg/ml, Fragrance.

Formulation 6

Purified Water, Glycerin, Nipagin M ™, TEA 99%, Irgasan DP300 ™, Promulgen D ™, Tegosoft OP ™, Blandol Mineral Oil, Shea Butter, GMS-SE, Lipovol Soy ™, Vitamin E Acetate, Nipasol M ™, Fragrance 700F48, Fucan/Galactan composition 0.1-99.9% of 5.5 mg/ml.

Formulation 7

Purified Water, Propylene Glycol, Magnesium Ascorbyl Phosphate, Nipagin M ™, Sodium Citrate, Irgasan DP300 ™, Promulgen D ™, Tegosoft OP ™, Blandol Mineral Oil, Shea Butter, GMS-SE, Lipovol Soy ™, Vitamin E Acetate, Nipasol M ™, Fragrance 700F47, Fucan/Galactan composition 0.1-99.9% of 5.5 mg/ml.

EXAMPLE 9

Sensitive Skin Cream

| Ingredients | Wt % |
|---|---|
| Demineralized water | QSP 100 |
| Xanthan Gum | 0.15 |
| Phenoxyethanol (and) Methylparaben (and) Butylparaben (and) Ethylparaben (and) Propylparaben | 0.60 |
| Chlorphenesin | 0.20 |
| Glycerin | 3.00 |
| Cetearyl Alcohol (and) Cetearyl Glucoside | 4.00 |
| Caprylic/Capric Triglyceride | 2.00 |
| Jojoba Esters | 0.50 |
| Squalane | 3.00 |
| Shea Butter | 0.50 |
| Wheat Germ oil | 1.00 |
| Onager oil | 1.00 |
| *Macadamia Ternifolia* Seed oil | 1.00 |
| PEG-8 (and) Tocopherol (and) Ascorbyl Palmitate (and) Ascorbic Acid (and) Citric Acid | 0.10 |
| Tocopheryl Acetate | 0.20 |
| Aluminium Starch Octenyl-Succinate | 1.50 |
| Aldavine ™ (fucans/galactans 10/1 0.1-99.9%) | 1.00-5.00 |
| Fragrance | 0.30 |
| Citric acid | 0.04 |

EXAMPLE 10

Firming Cream

| Ingredients | Wt % |
| --- | --- |
| Demineralized water | QSP 10 |
| Glycerin | 3.00 |
| Phenoxyethanol (and) Methylparaben (and) Butylparaben (and) Ethylparaben (and) Propylparaben | 0.60 |
| Chlorphenesin | 0.20 |
| Cetearyl Alcohol (and) Cetearyl Glucoside | 6.00 |
| Caprylic/Capric Triglyceride | 5.00 |
| Squalane | 3.00 |
| Dimethicone | 1.00 |
| Shea Butter | 2.00 |
| Cetearyl Alcohol | 1.00 |
| Hydrogenated coco-glyceride | 3.00 |
| Cetyl Acetate (and) Acetylated lanaolin Alcohol | 0.50 |
| Cetyl Alcohol | 2.00 |
| PEG-8 (and) Tocopherol (and) Ascorbyl Palmitate (and) Ascorbic acid (and) Citric acid | 0.10 |
| Aldavine ™ (fucans/galactans 10/1 0.1-99.9%) | 1.00-5.00 |
| Polyacrylamide (and) C13-14 isoparaffin (and) Laureth-7 | 0.30 |
| Fragrance | 0.30 |

EXAMPLE 11

Firming Serum-Lotion

| Ingredients | Wt % |
| --- | --- |
| Demineralized water | QSP 100 |
| Hydroxyethylcellulose | 0.40 |
| Glycerin | 3.00 |
| Phenoxyethanol | 0.40 |
| Benzyl alcohol | 0.60 |
| Carbomer | 0.05 |
| Sodium Hydroxide (10% aqueous solution) | 0.05 |
| Ethylhexyl Methoxycinnamate (and) Butyl Methoxydibenzoylmethane (and) Ethylhexyl Salicylate (and) PPG-26-Buteth-26 (and) PEG-40-Hydrogenated Castor oil | 0.50 |
| Bis-PEG-18 Methyl Ether Dimethyl Silane | 2.00 |
| Aldavine ™ (fucans/galactans 10/1 0.1-99.9%) | 1.00-5.00 |
| Fragrance | 0.10 |
| PPG-26-Buteth-26 (and) PEG-40-Hydrogenated Castor oil | 0.20 |
| Blue 1 (0.1% aqueous solution) | 0.09 |

EXAMPLE 12

Anti-Age Mask

| Ingredients | Wt % |
| --- | --- |
| Demineralized water | QSP100 |
| Glycerin | 3.00 |
| Phenoxyethanol (and) Methylparaben (and) Butylparaben (and) Ethylparaben (and) Propylparaben | 0.60 |
| Chlorphenesin | 0.20 |
| Cetearyl Alcohol (and) Cetearyl Glucoside | 6.00 |
| Caprylic/Capric Triglyceride | 5.00 |
| Squalane | 3.00 |
| Dimethicone | 1.00 |
| Shea Butter | 2.00 |
| Cetearyl Alcohol | 1.00 |
| Hydrogenated coco-glyceride | 3.00 |
| Cetyl Acetate (and) Acetylated lanolin Alcohol | 0.50 |
| Cetyl Alcohol | 2.00 |
| Kaolin | 5.50 |
| PEG-8 (and) Tocopherol (and) Ascorbyl Palmitate (and) Ascorbic acid (and) Citric acid | 0.10 |
| Aldavine ™ (fucans/galactans 10/1 0.1-99.9%) | 1.00-5.00 |
| Polyacrylamide (and) C13-14 isoparaffin (and) Laureth-7 | 0.30 |
| Fragrance | 0.30 |
| Citric Acid (10% aqueous solution) | 0.07 |

EXAMPLE 13

After-Sun Cream

| Ingredients | Wt % |
| --- | --- |
| Demineralized water | QSP 100 |
| Ethylhexyl Methoxycinnamate (and) Butyl Methoxydibenzoylmethane (and) Ethylhexyl Salicylate (and) PPG-26-Buteth-26 (and) PEG-40-Hydrogenated Castor oil | 0.50 |
| Carbomer | 0.50 |
| Tromethamine | 0.30 |
| Demineralized Water | 2.00 |
| Glycerin | 3.00 |
| Butylene Glycol | 3.00 |
| Phenoxyethanol (and) Methylparaben (and) Butylparaben (and) Ethylparaben (and) Propylparaben | 0.70 |
| Chlorphenesin | 0.25 |
| PEG-20 Methyl Glucose Sesquistearate | 3.00 |
| Polydecene | 10.00 |
| Sweet Almond oil | 5.00 |
| PEG-8 (and) Tocopherol (and) Ascorbyl Palmitate (and) Ascorbic Acid (and) Citric Acid | 0.05 |
| Aldavine ™ (fucans/galactans 10/1 0.1-99.9%) | 1.00-5.00 |
| Polyacrylamide (and) C13-14 Isoparaffin (and) Laureth-7 | 0.10 |
| Fragrance | 0.30 |

EXAMPLE 14

After Shave Balm

| Ingredients | Wt % |
| --- | --- |
| Distilled/Deionized Water | QSP 100 |
| Ethylhexyl Methoxycinnamate (and) Butyl Methoxydibenzoylmethane (and) Ethylhexyl Salicylate (and) PPG-26-Buteth-26 (and) PEG-40-Hydrogenated Castor oil | 0.50 |
| Acrylates/C10-30 Alkyl Acrylate Crosspolymer | 0.30 |
| Satiaxane CX 91 | 0.20 |
| Glycerin | 3.00 |
| Phenoxyethanol (and) Methylparaben (and) Butylparaben (and) Ethylparaben (and) Propylparaben | 0.60 |
| Chlorphenesin | 0.20 |
| Glyceryl Polymethacrylate (and) Propylene Glycol | 5.00 |
| Aluminium Starch octenylsuccinate | 1.00 |
| Squalane | 2.00 |
| Polyacrylamide (and) C13-14 isoparaffin (and) Laureth-7 | 0.27 |
| Demineralized water | 3.00 |
| Tromethamine | 0.30 |
| Cyclopentasiloxane (and) Propylene glycol | 1.00 |
| Aldavine ™ (fucans/galactans 10/1 0.1-99.9%) | 1.00-5.00 |

EXAMPLE 15

Hair Repairing Mask

| Ingredients | Wt % |
| --- | --- |
| Demineralized water | QSP 100 |
| Propylene glycol | 3.00 |
| DMDM Hydantoin (and) Iodopropynyl Butylcarbamate | 0.10 |
| Cetearyl Alcohol (and) Cetearyl Glucoside | 6.00 |
| Phenyl Trimethicone | 2.00 |
| Stearyl Alcohol | 3.00 |
| Cetrimonium Chloride | 1.00 |
| Aldavine ™ (fucans/galactans 10/1 0.1-99.9%) | 1.00-5.00 |
| Citric Acid (10% aqueous solution) | 0.23 |
| Fragrance | 0.30 |

EXAMPLE 16

Hand Cream

| Ingredients | Wt % |
| --- | --- |
| Demineralized water | QSP 100 |
| Carbomer | 0.15 |
| Xanthan Gum | 0.20 |
| Sodium hydroxide (10% aqueous solution) | 0.15 |
| Disodium EDTA | 0.10 |
| Demineralized water | 2.00 |
| Glycerin | 5.00 |
| Phenoxyethanol (and) Methylparaben (and) Butylparaben (and) Ethylparaben (and) Propylparaben | 0.80 |
| Chlorphenesin | 0.28 |
| Glyceryl Stearate (and) PEG-100 Stearate | 5.00 |
| PPG-15 stearyl Ether | 2.00 |
| Shea Butter | 2.00 |
| Cetyl Alcohol | 2.50 |
| C12-15 Alkyl Benzoate | 3.00 |
| Cyclomethicone | 2.00 |
| PEG-8 (and) Tocopherol (and) Ascorbyl Palmitate (and) Ascorbic acid (and) Citric acid | 0.08 |
| Aldavine ® (fucans/galactans 10/1 0.1-99.9%) | 1.00-5.00 |
| Polyacrylamide (and) C13-14 isoparaffin (and) Laureth-7 | 0.79 |
| Fragrance | 0.20 |

EXAMPLE 17

Heavy Legs Emulsion

| Ingredients | Wt % |
| --- | --- |
| Demineralized water | QSP 100 |
| Tetrasodium EDTA | 0.10 |
| Carbomer | 0.30 |
| Glycerin | 4.00 |
| Phenoxyethanol (and) Methylparaben (and) Butylparaben (and) Ethylparaben (and) Propylparaben | 0.60 |
| Chlorphenesin | 0.20 |
| Butylene Glycol | 3.00 |
| Cetearyl isononanoate | 4.00 |
| Dimethicone | 3.00 |
| Tromethamine | 0.25 |
| Demineralized water | 2.00 |
| Ethylhexyl Methoxycinnamate (and) Butyl Methoxydibenzoylmethane (and) Ethylhexyl Salicylate (and) PPG-26-Buteth-26 (and) PEG-40-Hydrogenated Castor oil | 0.50 |
| Polyacrylamide (and) C13-14 isoparaffin (and) Laureth-7 | 2.00 |
| Menthoxypropanediol | 0.20 |
| Aldavine ™ (fucans/galactans 10/1 0.1-99.9%) | 1.00-5.00 |
| Polysorbate 20 | 1.00 |
| Fragrance | 0.30 |

EXAMPLE 18

Lips Emulsion

| Ingredients | Wt % |
| --- | --- |
| Demineralized water | QSP 100 |
| Disodium EDTA | 0.15 |
| Xanthan Gum | 0.30 |
| Methylparaben (and) Ethylparaben (and) Butylparaben (and) Propylparaben (and) isobutylparaben | 0.30 |
| Chlorphenesin | 0.25 |
| Glycerin | 15.00 |
| Cetearyl Alcohol (and) Cetearyl Glucoside | 5.00 |
| Glyceryl Stearate (and) PEG-100 Stearate | 2.00 |
| Cetyl Alcohol | 2.00 |
| Squalane | 7.00 |
| Jojoba seed oil | 3.00 |
| Camelina Sativa seed oil | 5.00 |
| Shea Butter | 7.00 |
| Tocopheryl Succinate | 0.15 |
| Camelina Sativa Seed oil | 1.00 |
| Cyclomethicone | 3.00 |
| PEG-8 (and) Tocopherol (and) Ascorbyl Palmitate (and) Ascorbic Acid (and) Citric Acid | 0.10 |
| Tocopheryl Acetate | 0.25 |
| Aldavine ™ (fucans/galactans 10/1 0.1-99.9%) | 1.00-5.00 |
| Fragrance | 0.10 |
| Sodium Hydroxyde (10% aqueous solution) | 0.042 |

EXAMPLE 19

Slimming Gel

| Ingredients | Wt % |
| --- | --- |
| Demineralized water | QSP 100 |
| Acrylates/C10-30 Alkyl Acrylate Crosspolymer | 0.25 |
| Tromethamine | 0.15 |
| Demineralized water | 2.00 |
| Glycerin | 3.00 |
| Benzyl Alcohol | 0.60 |
| Phenoxyethanol | 0.40 |
| Ethylhexyl Methoxycinnamate (and) Butyl Methoxydibenzoylmethane (and) Ethylhexyl Salicylate (and) PPG-26-Buteth-26 (and) PEG-40-Hydrogenated Castor oil | 0.50 |
| Aldavine ™ (fucans/galactans 10/1 0.1-99.9%) | 1.00-5.00 |
| Fragrance | 0.20 |

-continued

| Ingredients | Wt % |
|---|---|
| Blue 1 (0.1% aqueous solution) | 0.50 |

EXAMPLE 20

Cleansing Cream

| Ingredients | Wt % |
|---|---|
| Glyceryl Stearate | 4.00 |
| Cetearyl Alcohol | 1.60 |
| Sodium Cocoyl Lactylate | 0.50 |
| Mineral Oil | 20.00 |
| Mineral Oil and Lanolin Alcohol | 4.00 |
| Distilled/Deionized Water | 64.70 |
| Aldavine ™ (fucans/galactans 10/1 0.1-99.9%) | 1.00-5.00 |
| Glycerine | 5.00 |
| Preservative | 0.20 |

Using the FLMW/GHMW (10/1) composition in a cosmetic formulation will potentially provide skin with the tools it needs to protect the integrity of the microcapillaries. By inhibiting the excessive production of VEGF and $PGE_2$, the present composition aims at preserving a better skin health. This phenomenon will help protect and maintain the integrity of the extra cellular matrix (ECM) and prevent or alleviate skin disorders as exemplified but not limited to: those caused by UV and pollutants exposure, sensitive skin, stress, psoriasis, acne, rosacea, telangiectasia, skin cancer, and skin aging.

The compositions may be improved by using polysaccharides having at least a portion of mineralized polysaccharides, namely FHMW-M, which has for effect to increase the inhibition of $PGE_2$.

The compositions may be administered topically in a suitable therapeutic formulation to animals; and humans as a bioactive agent. A dosage regimen ranging from 0.1 to 25% of 5.5 mg/ml for instance, preferably from 1 to 10%, more preferably from 1 to 5% is envisaged, achieving an effective dose at the site of inflammation (local or in situ effect).

Additionally, the bioactive agent may be complexed with a variety of well established compounds or compositions which enhance stability or pharmacological properties such as half-life. It is evident in the art that the therapeutic, bioactive composition may be delivered by topical application or any other effective means or routes which could be used for treating problems involving:

Psoriasis: Since psoriasis appears to be a multifactorial disease, it is assumed that the response of the patients depends on the importance of the involvement of components like angiogenesis and inflammation in the establishment and in the perpetuation of this condition. Moreover excess VEGF in skin may provide just such a predisposition by inducing a vascular inflammatory response that then predisposes to more widespread tissue inflammation closely resembling the psoriatic state. The ability of VEGF to induce a psoriasiform phenotype suggests a new etiology and treatment approach for this disease that justify the used of the present composition in such disorder (Yu-Ping Xia, Baosheng Li, Donna Hylton, Michael Detmar, George D. Yancopoulos, and John S. Rudge 2003 Blood, 1 Jul. 2003, Vol. 102, No. 1, pp. 161-168)

Rosacea: A comprehensive review of this skin disorder by J. K. Wilkin (Arch. Dermatol. (1994) vol. 130, 359-362) indicates that tosacea develops as a combination of one or more of the following cutaneous stigmata: flushing, erythema, telangiectasia, facial edema, papules, pustules, ocular lesions and rhinophyma, depending on the disorder stage development.

Hence, erythema and telangiectasia are vascular disorders, and other characteristics of these disorders that are not of a vascular nature, may derive from a vascular disturbance. The erythema is the first symptom of rosacea to be observed and is defined by an increased number of erythrocytes in a mildly inflamed vasculature. Furthermore a dermal cellulitis may appear as a result of an extravascular fluid accumulation consequent to irritant factors. The edema is the result of an increased extravasation along with a decreased fluid removal by lymphatic vessels. Decreased lymphatic activity appears to be consequent to lymphatic damage occurring during cellulitis. Rhinophyma may be explained by the observation that chronic cutaneous edema is frequently followed by connective tissue hypertrophy and fibroplasia and may also be due to factor XIII expression. It has been further emphasized that the elastin network that surrounds the lymphatic system in the skin serves two important functions. First, it is a tethering that permits the lymphatic endothelium to be sensitive to the volume of fluids in the vicinity of the lymphatic vessels, so that any increase of volume results in greater tension on the anchoring filaments. Second, the elastin network provides a low-resistance pathway through the intersticium along which micromolecules pass to the lymphatic vessels. Elastin degeneration due to actinic exposure is probably a common cause of lymphatic failure in rosacea.

During inflammation, neutrophils are recruited and exacerbate the rapid degradation of a variety of extracellular matrix macromolecules, especially elastin. Neutrophil elastase degrades type IV collagen in the extracellular matrix on which the integrity of the capillary walls depends. When lymphatic failure occurs, a sustained inflammation takes place. When lymphatic failure does not resolve the inflammation becomes self-sustained. The plasma proteins that accumulate in the sustained inflamed tissue appear to contribute to the fibroplasia, which underlies the development of rhinophyma.

Telangiectesia represents the latter phase of the vascular stage of rosacea. The mechanical integrity of the dermal connective tissue is reduced, allowing a passive dilation of the vasculature. The perivascular inflammatory cells thus infiltrate and contribute to rosacea. Dilatation of both dermal blood vessels and lymphatics are prominent in rosacea. Angiogenesis may contribute to the telangiectasia. Angiogenesis depends on the space left between in a tissue where endothelial cells can grow. Edema reduces the tissue compactness, permitting vascularization. Since lymphatic failure results in sustained inflammatory response, the edema thus created would be one the feature that favors angiogenesis.

As already mentioned above, it appears that rosacea is initiated by an inflammatory reaction which does not resorb with time. Since the polysaccharide compositions of the present invention comprise a plurality of biological activities such as an anti-inflammatory activity and since it inhibits VEGF secretion, it is contemplated that the polysaccharide compositions of the present invention will have an effect on all skin diseases involving one or more etiologies related to these biological activities. The compositions of the present invention comprise a plurality of active ingredients and as such will be effective in treating mono- as well as in plurifactorial diseases or disorders. The treatment of rosacea is a typical example of such a plurifactorial disorder wherein inflammation, and extravasation occur.

Other or similar compositions can also be conceived to be used in a method for soothing skin or for reducing inflammation in mammalian skin. Inflammation can be caused by various agents such as chemical irritant, physical abrasion and exposure to ultraviolet radiation. Compositions and methods for inhibiting collagenase in skin are also contemplated. Collagenase and inflammation are linked to premature aging (degradation of collagen), and therefore the antagonist activities recovered in the polysaccharide compositions could also be put to contribution in compositions and methods for retarding premature aging, and for regulating wrinkles or atrophy in mammalian skin. As causes of wrinkles or atrophy are listed, by way of examples, age, exposure to ultraviolet radiation or to environmental pollutant. Topical compositions may comprise an effective amount of polysaccharide composition, to be determined for each specific application.

Acne: In acne pathogenesis, *Propionibacterium acnes* is known to induce inflammatory mediators, Such as IL-8. This cytokine may be directly implicated in the inflammatory response by its capacity to attract, by a chemotactic response, inflammatory cells to the site of infection. IL-8 can also be implicated in the development of acne lesions (Schaller M, Loewenstein M, Borelli C, Jacob K, Vogeser M, Burgdorf W H C, Plewig G. Induction of a chemoattractive proinflammatory cytokine response after stimulation of keratinocytes with *Propionibacterium acnes* and coproporphyrin III. Br J. Dermatol. 2005 July; 153(1):66-71.). According to this pathogenesis, topical compositions may be conceived to be used to reduce inflammatory response and acne lesions.

In general, these compositions may contain from about 0.1 to about 30 weight percent of a polysaccharide compositions and from about 70 to 99.9 weight percent of a pharmaceutically acceptable vehicle. These compositions may contain an anti-oxidant, such as an agent which prevents the formation of lipid peroxides in skin. Examples of such an anti-oxidant are tocopherol, tocopherol derivatives, ascorbic acid, ascorbic acid derivatives and BHT. The compositions can be complemented with anti-inflammatory agents like a phospholipase A2 inhibitor or the botanically-derived anti-irritants cola, green tea and cartilage extracts. Topical compositions may take diverse forms such as solutions, suspensions, lotions, tinctures, gels, creams, sprays, emulsions, sticks, ointments or liposomes. Other cosmetic applications include dark circle around the eyes and skin barrier function, care of skin photodamaging, sensitive skin, erythema, rosacea, teleangiectasia, actinic elastosis, psoriasis, and acne.

Although the present invention has been described hereinabove by way of specific embodiments thereof, it can be modified, without departing from the spirit and nature of the subject invention as defined in the appended claims.

The invention claimed is:

1. A method for inhibiting the release of one or more of IL-8, PGE2 and VEGF by a cell activated during an inflammatory process, said method comprising administering to said cell an anti-inflammatory polysaccharide composition comprising brown algae fucans and red algae galactans, wherein the fucans and the galactans in said composition are present in a ratio ranging from about 2.5 fucans/1 galactan (w/w) to about 40 fucans/1 galactan (w/w);
   said galactans having:
       (i) an average molecular weight higher than about 100 kDa;
       (ii) a galactose content ranging from about 30 to about 40% of dry weight of the galactans;
       (iii) a sulfate content ranging from about 20 to about 35% of dry weight of the galactans; and
       (iv) an uronic acid content ranging from about 1 to about 5% of dry weight of the galactans;
   and said fucans having:
       (v) an average molecular weight ranging from about 5 kDa to about 100 kDa;
       (vi) a fucose content ranging from about 20 to about 35% of dry weight of the fucans;
       (vii) a sulfate content ranging from about 15 to about 25% of dry weight of the fucans; and
       (viii) an uronic acid content ranging from about 10 to about 29% of dry weight of the fucans,
   wherein the ratio of fucans to galactans in said composition enables a reduction in the cytotoxicity of said galactans.

2. The method of claim 1, wherein the release of IL-8, PGE2 and VEGF is from epithelial cells.

3. The method of claim 1, wherein the fucans increase the inhibition of inflammation.

4. The method of claim 1, wherein said red algae are *Asparagopsis armata*.

5. The method of claim 1, wherein said brown algae are *Ascophyllum nodosum*.

6. The method of claim 1, wherein the galactans have an average molecular weight of about 350 kDa.

7. The method of claim 1, wherein the galactans have a galactose content of about 37% of dry weight of the galactans.

8. The method of claim 1, wherein the galactans have an uronic acid content of about 3% of dry weight of the galactans.

9. The method of claim 1, wherein the galactans have a sulfate content of about 27% of dry weight of the galactans.

10. The method of claim 1, wherein the fucans have an average molecular weight ranging from about 5 kDa to about 25 kDa.

11. The method of claim 1, wherein the fucans and the galactans are present in a ratio of about 10 fucans/1 galactans (w/w) in the composition.

12. The method of claim 1, wherein the galactans comprise native galactans.

13. The method of claim 1, wherein the fucans comprise native fucans.

14. The method of claim 1, wherein the fucans comprise depolymerized fucans.

15. The method of claim 1, wherein the fucans comprise demineralized fucans.

16. The method of claim 1, wherein the galactans comprise demineralized galactans.

17. The method of claim 1, wherein said composition is administered topically.

18. The method of claim 17, for alleviating skin disorders or conditions caused by UV exposure, chemical stress, aggression from pollutants, exfoliating agents or skin irritants.

19. The method of claim 17, for reducing skin disorders or conditions caused by UV exposure, chemical stress, aggression from pollutants, exfoliating agents or skin irritants.

20. An anti-inflammatory composition comprising brown algae fucans and red algae galactans, wherein the ratio of brown algae fucans/red algae galactans in said composition is ranging from about 2.5/1 (w/w) to about 40/1 (w/w), said galactans having:
   (i) an average molecular weight higher than about 100 kDa;
   (ii) a galactose content ranging from about 30 to about 40% of dry weight of the galactans;
   (iii) a sulfate content ranging from about 20 to about 35% of dry weight of the galactans; and
   (iv) an uronic acid content ranging from about 1 to about 5% of dry weight of the galactans;

and said fucans having:
- (v) an average molecular weight ranging from about 5 kDa to about 100 kDa;
- (vi) a fucose content ranging from about 20 to about 35% of dry weight of the fucans;
- (vii) a sulfate content ranging from about 15 to about 25% of dry weight of the fucans; and
- (viii) an uronic acid content ranging from about 10 to about 29% of dry weight of the fucans;

wherein the ratio of fucans to galactans in said composition enables a reduction in the cytotoxicity of said galactans.

21. The composition of claim 20, wherein the galactans have an average molecular weight of about 350 kDa.

22. The composition of claim 20, wherein the galactans have a galactose content of about 37% of dry weight of the galactans.

23. The composition of claim 20, wherein the galactans have an uronic acid content of about 3% of dry weight of the galactans.

24. The composition of claim 20, wherein the galactans have a sulfate content of about 27% of dry weight of the galactans.

25. The composition of claim 20, wherein the fucans have an average molecular weight ranging from about 5 kDa to about 25 kDa.

26. The composition of claim 20, the ratio of brown algae fucans/red algae galactans being of 10/1.

27. The composition of claim 20, the galactans having a molecular weight of about 350 kDa, and the fucans having a molecular weight ranging from about 15 kDa and about 25 kDa.

28. The composition of claim 20, wherein the brown algae is *Ascophyllum nodosum*.

29. The composition of claim 20, wherein the red algae is *Asparagopsis armata*.

30. The composition of claim 20, wherein the galactans comprise native galactans.

31. The composition of claim 20, wherein the fucans comprise native fucans.

32. The composition of claim 20, wherein the fucans comprise depolymerized fucans.

33. The composition of claim 20, wherein the fucans comprise demineralized fucans.

34. The composition of claim 20, wherein the galactans comprise demineralized galactans.

35. The composition of claim 20, which is a topical composition.

36. The composition of claim 35, which is a cosmetic composition.

37. The method of claim 1, wherein the cell is within a subject.

38. The method of claim 37, wherein the polysaccharide composition is topically administered to the subject.

39. The method of claim 38, wherein the subject is a human affected by skin disorders or conditions caused by UV exposure, chemical stress, aggression from pollutants, exfoliating agents or skin irritants.

40. The composition of claim 20, wherein the fucans have an average molecular weight ranging from about 5 kDa to about 25 kDa.

* * * * *